(12) United States Patent
Zarrabian

(10) Patent No.: US 11,137,349 B2
(45) Date of Patent: Oct. 5, 2021

(54) APPARATUS AND METHOD FOR DETECTING PHASE CHANGES IN A FLUID USING SPECTRAL RECOGNITION

(71) Applicant: Sohrab Zarrabian, Gaithersburg, MD (US)

(72) Inventor: Sohrab Zarrabian, Gaithersburg, MD (US)

( * ) Notice: Subject to any disclaimer, the term of this patent is extended or adjusted under 35 U.S.C. 154(b) by 196 days.

(21) Appl. No.: 16/570,709

(22) Filed: Sep. 13, 2019

(65) Prior Publication Data

US 2020/0088631 A1 Mar. 19, 2020

Related U.S. Application Data

(60) Provisional application No. 62/731,901, filed on Sep. 15, 2018.

(51) Int. Cl.
| | | |
|---|---|---|
| *G01N 21/69* | (2006.01) | |
| *G01J 3/02* | (2006.01) | |
| *G01N 21/3554* | (2014.01) | |
| *G01N 21/25* | (2006.01) | |
| *G01N 21/3504* | (2014.01) | |
| *G01N 21/41* | (2006.01) | |
| *G02B 6/02* | (2006.01) | |

(52) U.S. Cl.
CPC ....... *G01N 21/3554* (2013.01); *G01N 21/255* (2013.01); *G01N 21/3504* (2013.01); *G01N 21/412* (2013.01); *G02B 6/02076* (2013.01)

(58) Field of Classification Search
CPC .......... G01N 7/00; G01N 21/69; G01N 21/67; G01N 21/718; G01N 21/8507; G01N 30/00; G01N 5/00; G01N 5/025; G01N 9/00; G01N 21/00; G01N 2021/1704; G01N 21/3554; G01N 21/3577; G01J 3/443; G01J 3/0208
See application file for complete search history.

(56) References Cited

U.S. PATENT DOCUMENTS

| 7,581,877 B1 | 9/2009 | Zarrabian | |
|---|---|---|---|
| 2004/0035183 A1* | 2/2004 | O'Brien | G01N 1/2202 |
| | | | 73/23.27 |
| 2004/0264901 A1 | 12/2004 | Tao et al. | |
| 2009/0216463 A1 | 8/2009 | Xie et al. | |
| 2015/0377776 A1 | 12/2015 | Xie | |

OTHER PUBLICATIONS

International Search Report and Written Opinion dated Nov. 14, 2019 by the International Searching Authority (European Patent Office) in PCT Application PCT/US2019/051191.

* cited by examiner

*Primary Examiner* — Don K Wong
(74) *Attorney, Agent, or Firm* — NovoTechIP International PLLC

(57) ABSTRACT

Systems and methods are described, and one method includes passing an optical beam through a volume of the gas to a reception surface, applying spectroanalysis to the optical beam received at the reception surface, and determining from the spectroanalysis whether a liquid is carried by the volume of the gas.

20 Claims, 20 Drawing Sheets

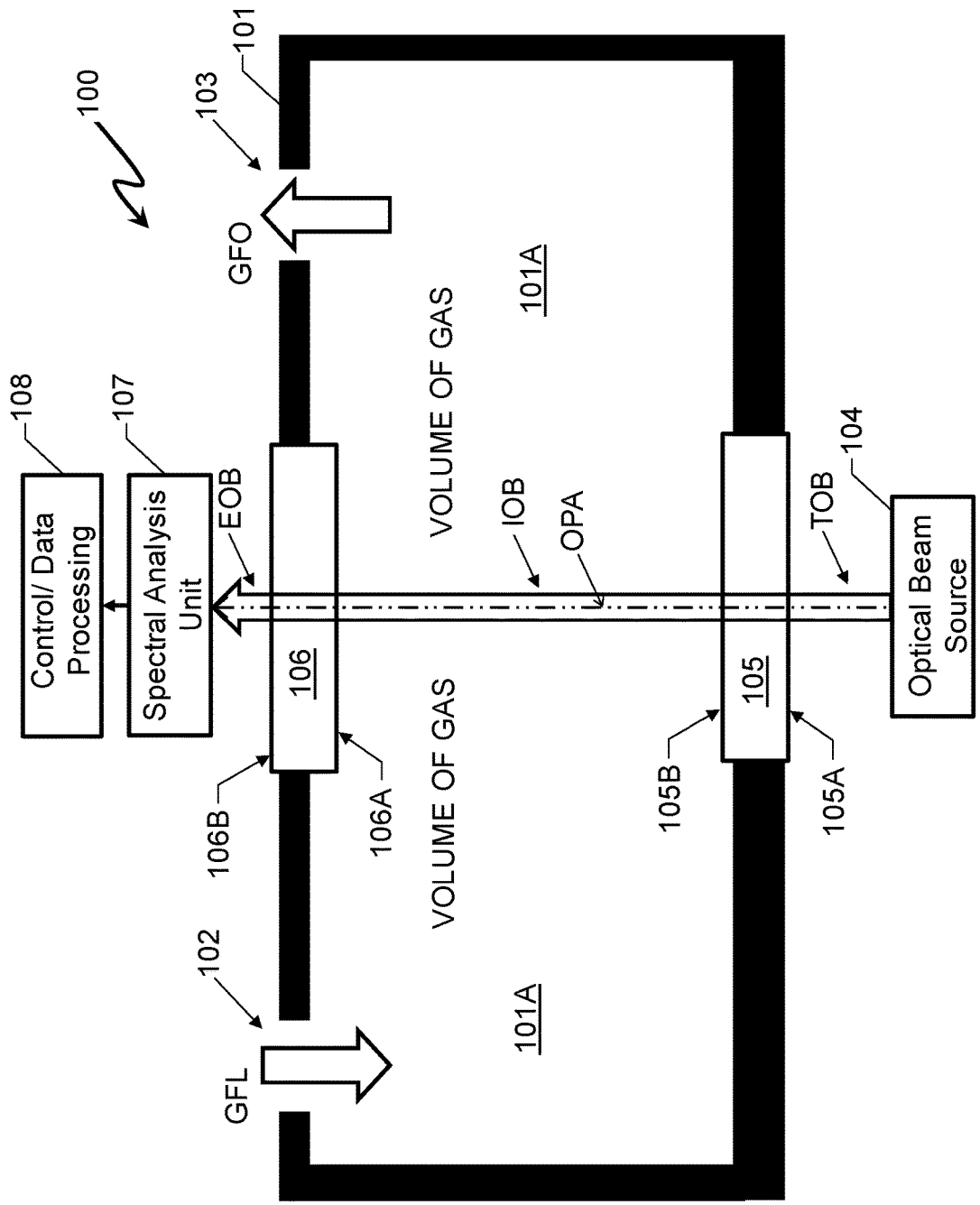

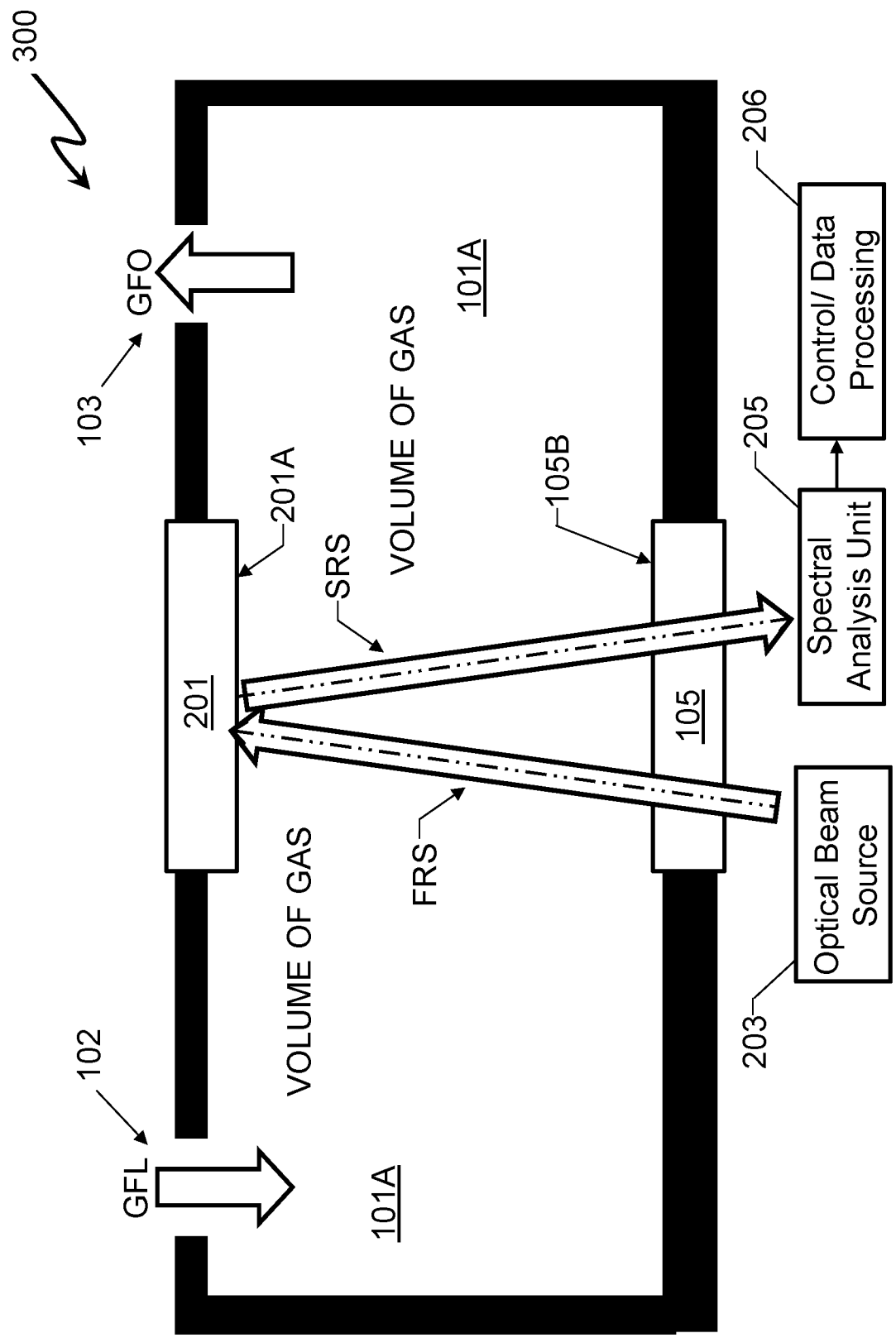

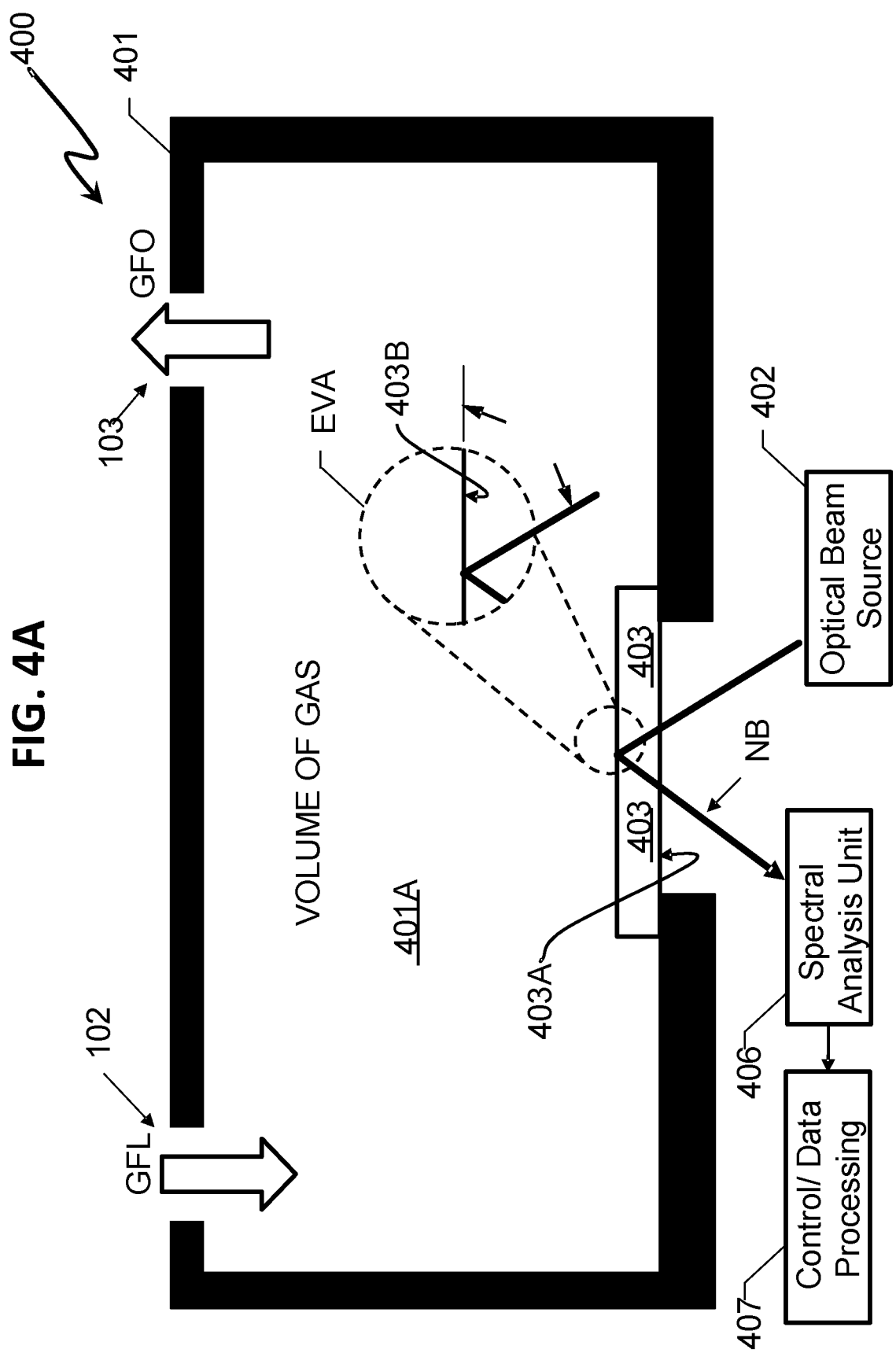

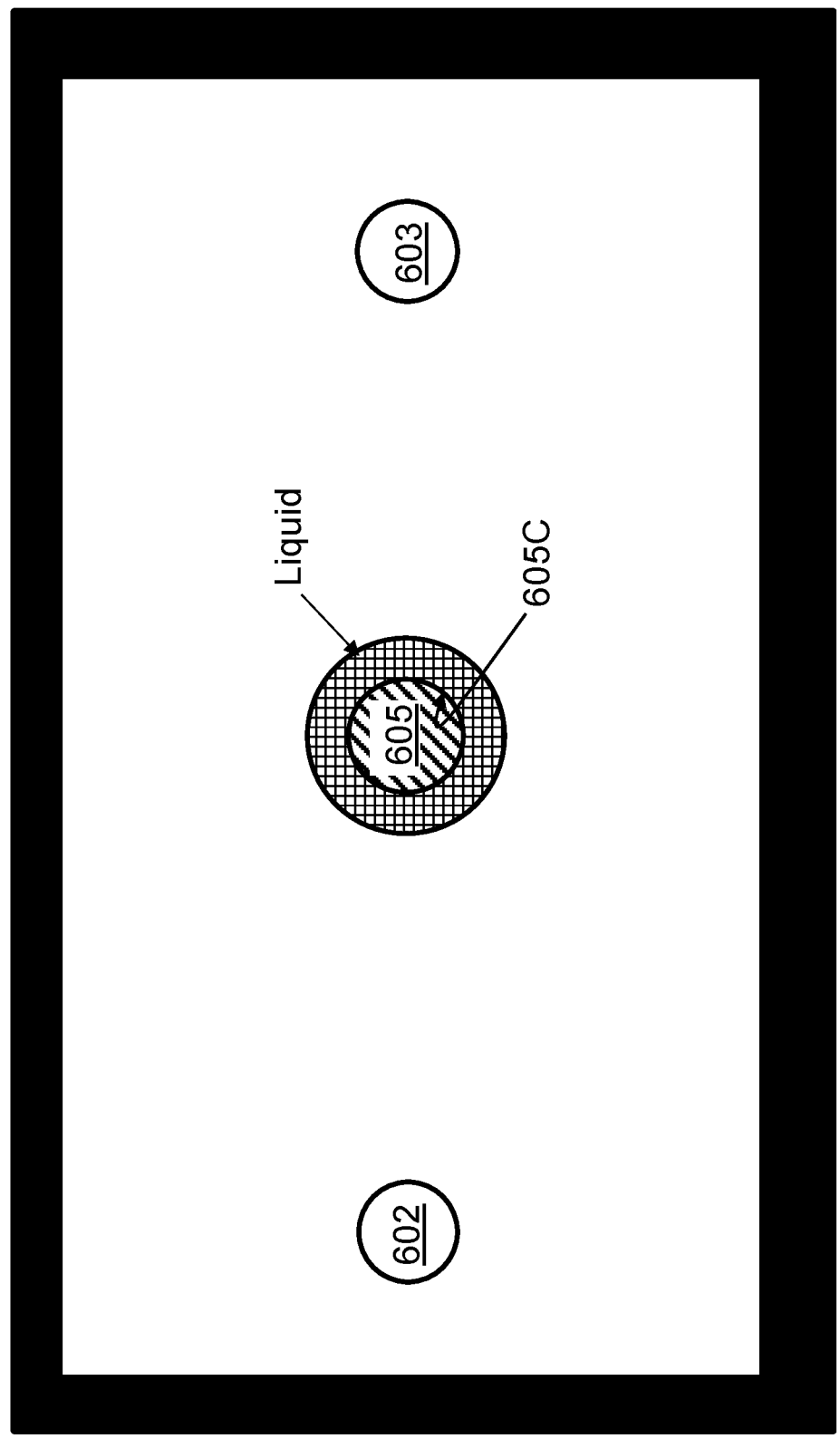

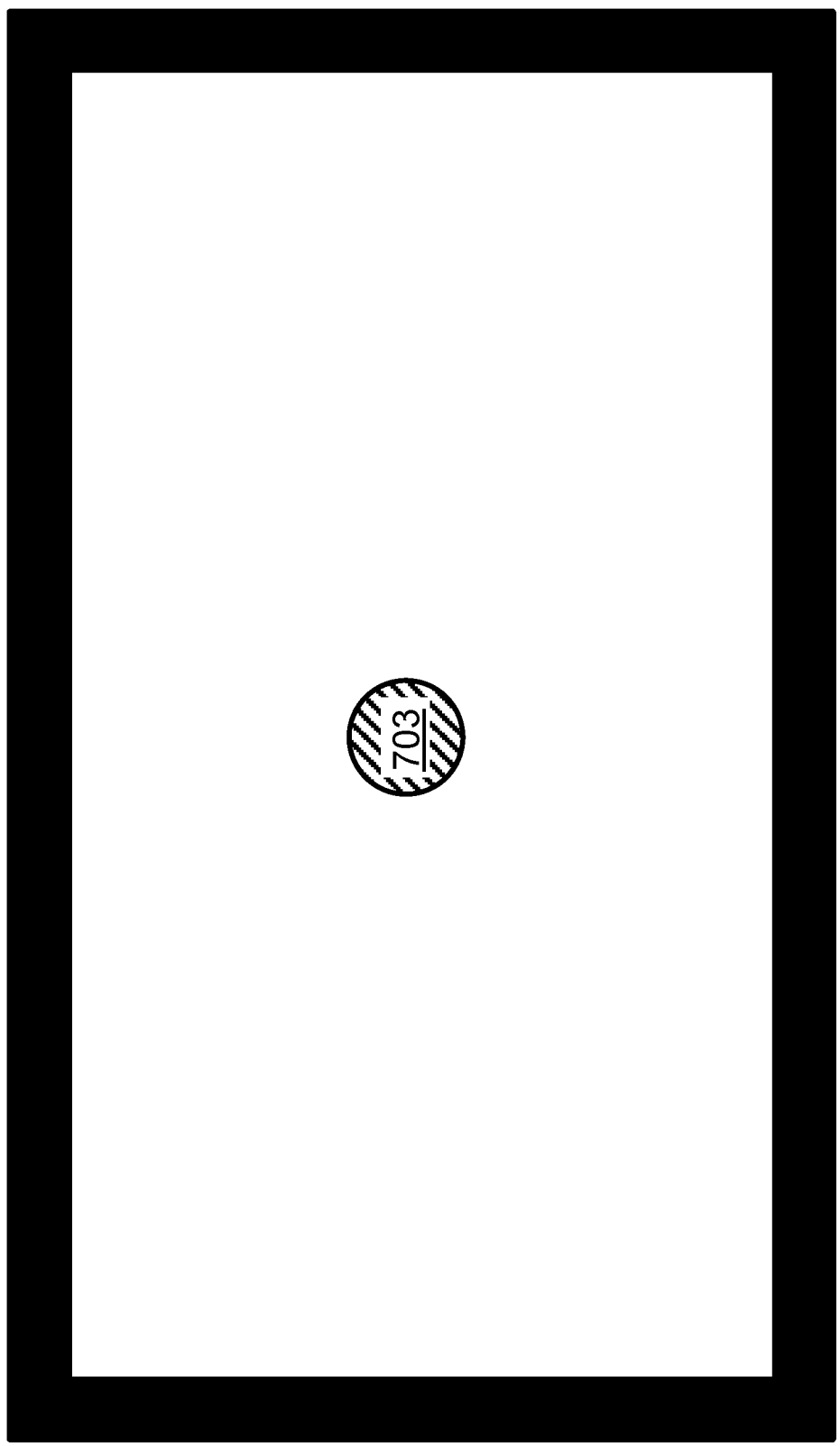

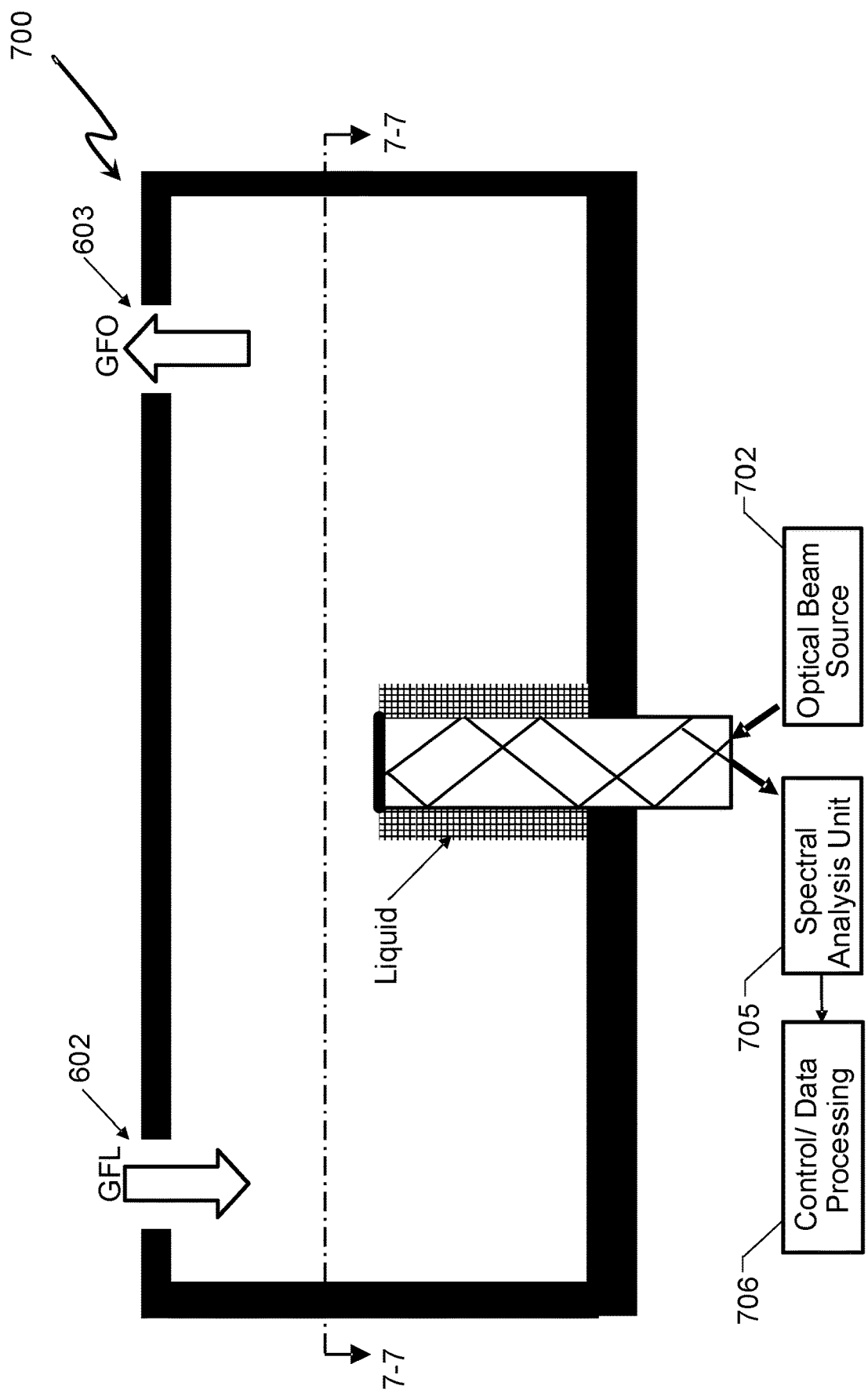

APPARATUS AND METHOD FOR DETECTING PHASE CHANGES IN A FLUID USING SPECTRAL RECOGNITION

CROSS REFERENCE TO RELATED APPLICATION

This application claims the benefit of priority from U.S. Provisional Patent Application Ser. No. 62/731,901, filed Sep. 15, 2018, and titled "APPARATUS AND METHOD FOR DETECTING PHASE CHANGES IN A FLUID USING SPECTRAL RECOGNITION," which is incorporated by reference herein in its entirety.

TECHNICAL FIELD

The disclosure relates generally to gas analysis and, more particularly, to detection of phase changes and of entrained liquids in a gas stream.

BACKGROUND

Presence of liquids in gas, even trace amounts, can be undesirable in various applications. For example, in the natural gas industry, operation of pipelines and measurement equipment can be compromised by liquids present in the gas. In the power generation industry, it can be desirable to know whether or not the fuel-gas has any entrained liquids, or if it is in the saturated state. Presence of liquids can also cause errors in the measurements of the quantity and quality of the gas.

In the petrochemical industry, the presence of liquids can be detrimental to various processes. Certain liquids can also be measured by vaporizing first into gaseous state and then measuring the properties of the gas. Incomplete vaporization, where some liquid remains in the liquid phase, can also be detrimental in such measurements. In the compressed air and in the gas industry, presence of liquids can damage compression equipment.

One technique for detecting liquids can be visual observation. Visual observation, though, requires presence of a human observer, either on site or, if a camera is positioned at the observation point, in front of a remote display screen. The human observer can be replaced a camera system and image-processing software. However, image-processing techniques are non-spectroscopic and as such cannot provide chemical composition information about the nature of the detected liquids. Image-processing techniques are also more susceptible to false positives and false negatives. Another technique for detecting presence of some liquids in a gas, is electro-chemical detection. However, this technique can have technical shortcomings. For example, electrochemical sensors can degrade over time and, may require re-calibration or re-setting. Also, for some applications, the electro-chemical sensors may not be sufficiently sensitive or specific.

Accordingly, what is needed is a low cost, reliable, accurate technique for detecting presence of liquid within gas in industries and applications, for example the natural gas industry, where such presence can be detrimental.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 1 is a cut-away view of an example implementation that transmits an optical beam through a gas volume, to a spectral analysis apparatus, for detection by a graphically illustrated processor, for systems and methods for detecting and monitoring liquids within a gas, according to various aspects.

FIG. 3A is a cut-away projection of one example variation of the FIG. 2A-2B implementation, providing one alternative multiple traversal propagation through the gas volume.

FIG. 4A is a cut-away view of one alternative implementation, which can propagate an optical beam through an optical element to an element surface facing the gas volume, with a refractive interface and corresponding beam induced evanescent tail that can vary with surface liquid, such that a non-absorbed optical beam signal can reflect back into and through the optical element to a spectral analysis and processing illustrated by a graphical schematic, for evanescent tail based monitoring and detection of liquids within a gas, in systems and methods according to various aspects.

FIG. 6D is the FIG. 6B cross-cut view of FIG. 6A structure, when in the FIG. 6C system state.

FIG. 7B is a cross-cut view of FIG. 7A structure, seen from the FIG. 7A cross-cut projection plane 7-7.

FIG. 7C illustrates the FIG. 7A implementation, at a system state indicating high liquid content in the gas volume, including liquid on the outer surface of the optical fiber.

DETAILED DESCRIPTION

Figure 2A:
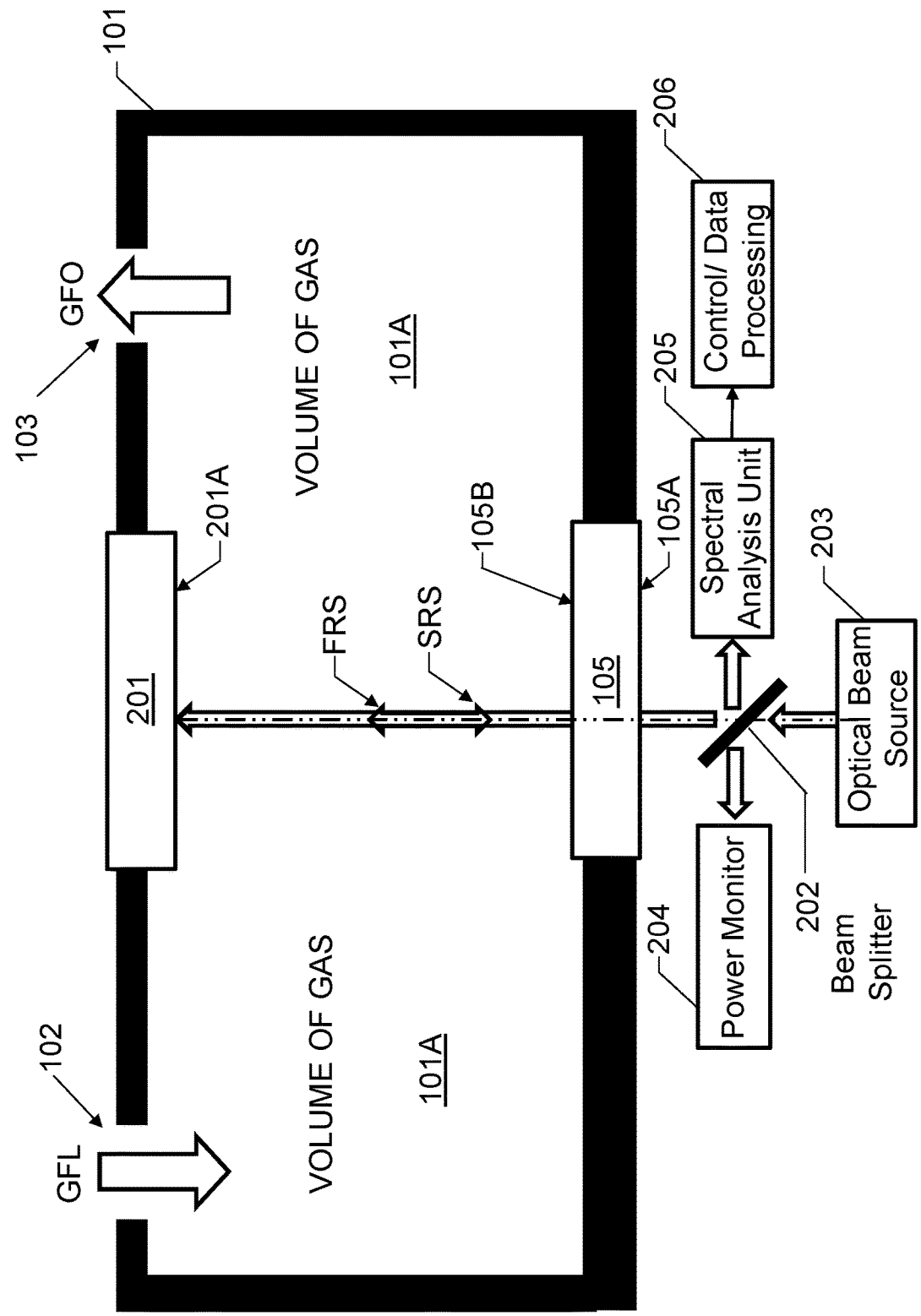
FIG. 2A is a cut-away projection of one example implementation, having an optical element surface facing a gas volume, that propagates the optical beam with multiple traversal through the gas volume, to a spectral analysis apparatus, for detection by a graphically illustrated processor, for systems and methods for detecting and monitoring liquids within a gas, according to various aspects.

In the following detailed description, numerous specific details are set forth by way of examples in order to provide a thorough understanding of the disclosed subject matter. It will be apparent to persons of ordinary skill, upon reading this current invention overcomes many of these shortcomings by detecting the phase change via a spectroscopic optical probe. The optical probe is spectroscopic and provides, not only information on the presence of liquids, but also their chemical nature. In this invention, an optical beam, preferably visible or infrared, interacts through a volume of gas and the output is spectrally monitored (FIGS. 1, 2A, 2B, 3A, and 3B). If the gas is devoid of liquids, the optical attenuation of the beam may be due to the molecules of the gas. This attenuation can have a spectral profile characteristic of the gas mixture. If there are any liquids present, the optical beam may still be attenuated by the gas molecules, but there can be additional attenuation. The extra attenuation can consist of two parts; 1) attenuation due to molecules of liquids absorbing the optical beam with a spectral profile characteristic of the liquid, and 2) attenuation due to optical scattering which is typically not spectral in nature. By monitoring the spectral content of the beam as it exits the gas cell, it can be determined a) whether or not there are any liquids present and b) what those liquids are.

Implementations can include different optical geometries, offering various advantages, as will be described in greater detail in reference to FIGS. 2A, 2B, 3A, 3B, 4A, 4B, 5A, 5B, 6A-6D, 7A, 7B, and 8. In such implementations, an optical element can be exposed to the gas on at least one of its surfaces. In one aspect, the refractive index of the optical element can be higher than the gas under analysis. An light beam, preferably visible or infrared, can be transmitted to pass through the optical element at an incidence angle. The critical angle is a function of the refractive index of the optical element, the refractive index of the gas under analysis, and the wavelength of the electromagnetic radiation.

As the light beam goes through internal reflection, some of the light will return. However, a small evanescent electromagnetic field can penetrate through the surface of the optical element into the gas. This evanescent field will interact with the gas under analysis and will be partially absorbed by the gas. The absorption takes place in wavelengths specific to the molecules present in the gas. In this configuration, the electromagnetic radiation interacts with a very small volume of the gas very close to the surface of the optical element.

Since gas is a sparse phase, though, the absorption of the electromagnetic radiation may be minimal. However, when liquids become present and cover the surface of the optical element, or are dispersed in the gas volume as small droplets, much greater absorption will take place. Implementations in accordance with this disclosure can provide monitoring of the change in the absorption of radiation and can therefore provide detection of the presence or formation of liquids in the gas phase.

One example method according to this disclosure can provide, among other features and advantages, a determination of whether a liquid is carried by a gas. Example operations can include passing an optical beam, from an optical source, through a volume of the gas, to a reception surface, applying a spectroanalysis to the optical beam as received at the reception surface, and outputting a corresponding spectroanalysis signal. Example operations can also include determining, based on the output spectroanalysis signal, whether a liquid is carried by the volume of the gas.

In an aspect, an optical beam traverses through a volume of gas, as illustrated by the FIG. 1 system 100. Additional implementations are illustrated by FIGS. 2A, 2B, 3A, and 3B. In another general implementation, an optical beam can be propagated through an optical element, to reflect one time from an interface between the optical element and the gas. The interface can be between the optical element material and the gas. If a liquid forms on the surface of the optical element, the interface will be between the optical element and the liquid. One further implementation can provide multiple reflections. Examples are described in reference to FIGS. 5, 6, 7, and 8.

To use the evanescent tail, implementation can expose the surface of an optical element to the fluid under test. The beam that has passed through the fluid under test can be directed, for example, as a reflected beam, into a spectral analysis device.

One example implementation of the spectral analysis device can be a traditional spectrometer. Another example implementation of the spectral analysis device can include one or more optical band-pass filters in combination with detectors to monitor specific spectral lines corresponding to the material of interest. The optical filters can be implemented, for example, as a gradient optical filter. The detectors can be implemented, for example, as a diode-array detector. Applying the spectroanalysis to the exit beam can include applying a Fourier Transform infrared Spectroscopy (FTIR).

Alternatively, if monitoring only for presence of liquid, then the total amount of reflected radiation or segments thereof can be monitored. If liquid forms within the monitored fluid, condensation of the liquid forms on the surface of the optical element exposed to the gas stream. Because the evanescent wave of the electrical field, resulting from the optical beam used, penetrates the material condensed on the surface, there will be optical absorption in certain spectral regions, characteristic of the condensed material. Implementations can measure this optical absorption and used it as an indication of presence of liquid. Implementations provide measurement of the optical absorption by monitoring the reflected optical radiation in specific spectral regions of interest. The electrical signals generated by the spectrometer or optical detectors can be provided to a micro-processor, such as the data processor/controller illustrated by FIG. 9, where it can be determined if liquids are present or not.

FIG. 1 is a cut-away view of one example implementation of system 100 that can transmit an optical beam through a gas volume, to a spectral analysis apparatus, for detection by a graphically illustrated processor, for systems and methods for detecting and monitoring liquids within a gas, according to various aspects. Referring to FIG. 1, the system 100 can include a chamber housing 101 enclosing a chamber interior 101A. A gas inflow port 102 can be formed through a wall (visible but not separately numbered) of the chamber housing 101, for gas inflow GFL into the chamber interior 101A, and a corresponding gas outflow port 103 can be formed to allow for gas outflow GFO from the chamber interior 101A. Implementations can include a gas inlet pipe (visible but not separately numbered) coupled to the gas inflow port 102, and a gas outlet pipe (visible but not separately numbered) coupled to the gas outflow port 103.

An optical beam transmitter or source 104 can be configured to transmit an output optical beam (TOB) toward a first or outer surface 105A of a first optical element 105, to pass into and through first optical element 105, exit from a second or an inward facing surface 105B of the a first optical element 105 into the chamber interior 101A, and propagate as interior optical beam (IOB), along an optical path (OPA) through a gas (e.g., air or natural gas) within the interior 101A, then out through a second optical element 106 to a receiving surface (visible, but not separately numbered) of a spectral analysis unit 107. Example implementations of the optical beam transmitter or source 104 can include, but are not limited to, a tungsten lamp, a thin-film resistor, a light-emitting diode, and a laser.

In an implementation, the first or outer surface 105A of the first optical element 105 can be a planar surface, and the optical beam source 104 can be configured to transmit the optical beam in a direction that can be normal to the outer planar surface 105A. The second optical element 106 can have an inner facing planar surface 106A and an opposite outer planar surface 106B.

Example implementations of the spectral analysis unit 107 are described in greater detail in later paragraphs. The spectral analysis unit 107 can output a spectral analysis signal (visible as an arrow, but not separately numbered), which can be received by a control/data processing resource or unit 108. It will be understood that "unit" is a virtual term, not necessarily descriptive or limiting as to technology, hardware architecture, or allocation or distribution of hardware. Contemplated implementations of the control/data processing unit 108 can include, for example, a cloud computing resource (not visible in FIG. 1). Another example implementation of the control/data processing unit 108 can include a programmable personal computer, having an interface to the spectral analysis unit 107.

It will be understood that implementations can include an absence of a heating mechanism for the first optical element 105, absence of a cooling mechanism for the first optical element 105, and absence of a heating and cooling mechanism for the second optical element 106.

In one example operation, the optical beam source 104 can operate continuously. In an aspect, though, the spectral analysis unit 107 can be configured to operate periodically, e.g., to generate a spectral measurement data set periodically. The length of the period, e.g., in second, minutes, or hours, i.e., the frequency of performing spectral measurement, can be application-specific. In another example operation, the optical beam source 104 can operate periodically, for example, synchronized with the period (or frequency) of the spectral analysis unit 107. In an aspect, the control/data processing apparatus 108 can be operated or activated periodically, for example, synchronized with the period of the spectral analysis unit 107. In one example implementation, the control/data processing apparatus 108 can be a virtual feature, implemented, for example, as a portion of a shared computation resource or capability. In one specific, but non-limiting configuration, the FIG. 1 system, 100 can be configured to apply a measurement, the measurement including passing the optic beam from the optical beam source 102, through the first optical element 105, and through the gas in the interior of the through the interior 101A to the second optical element 106 for another duration of time, and correspondingly repeating the spectroanalysis. The system 100 can be configured to determine, based on the output spectroanalysis signal corresponding to the measurement, whether the liquid is carried by the volume of gas; and repeating the performing the measurement and the corresponding determining, based on the measurement's output spectroanalysis signal, until the determining determines the liquid is carried by the volume of gas. In an aspect, no temperature modification is applied to the propagation path during the repeating the performing the measurement and, at each repeat, determining based on the measurement output spectroanalysis signal, whether the liquid is carried by the volume of gas.

FIG. 2A is a cut-away projection of one example implementation of a system 200, which can be a modification of the FIG. 1 system 100. An implementation of the system 200 can be formed by replacing the FIG. 1 second optical element 106 with a mirror structure 201, having a mirror face 201A facing the chamber interior 101A, and inserting a beam splitter 202 in the optical path between an optical beam source 203 and the first face 105A (outward facing surface) of the first optical element 105. The optical beam can propagate as a first ray segment FRS from the optical beam source 203 through the beam splitter 202, through first optical element 105, and through the volume of gas to the mirror face 201A, and return as a second ray segment SRS from the mirror face 201A, through the volume of gas, through the first optical element 105, to the beam splitter 202. In the implementation visible in FIG. 2A the optical beam is normal to the first optical element 105 surfaces 105A and 105B, and normal to the mirror face 201A, and the first ray segment FRS and the second ray segment SRS are therefore parallel to one another. The optical beam source 203 can be identical to the FIG. 1 optical beam source 104. Alternatively, the optical beam source 203 can be a higher power device, or can include a readily adjustable output power, or both. In an aspect, a power monitor 204 can be included. The spectral analysis unit 205 can be the same as the spectral analysis unit 107, and the control processor 206 can be the same as the control/data processing apparatus 108.

Figure 2B:
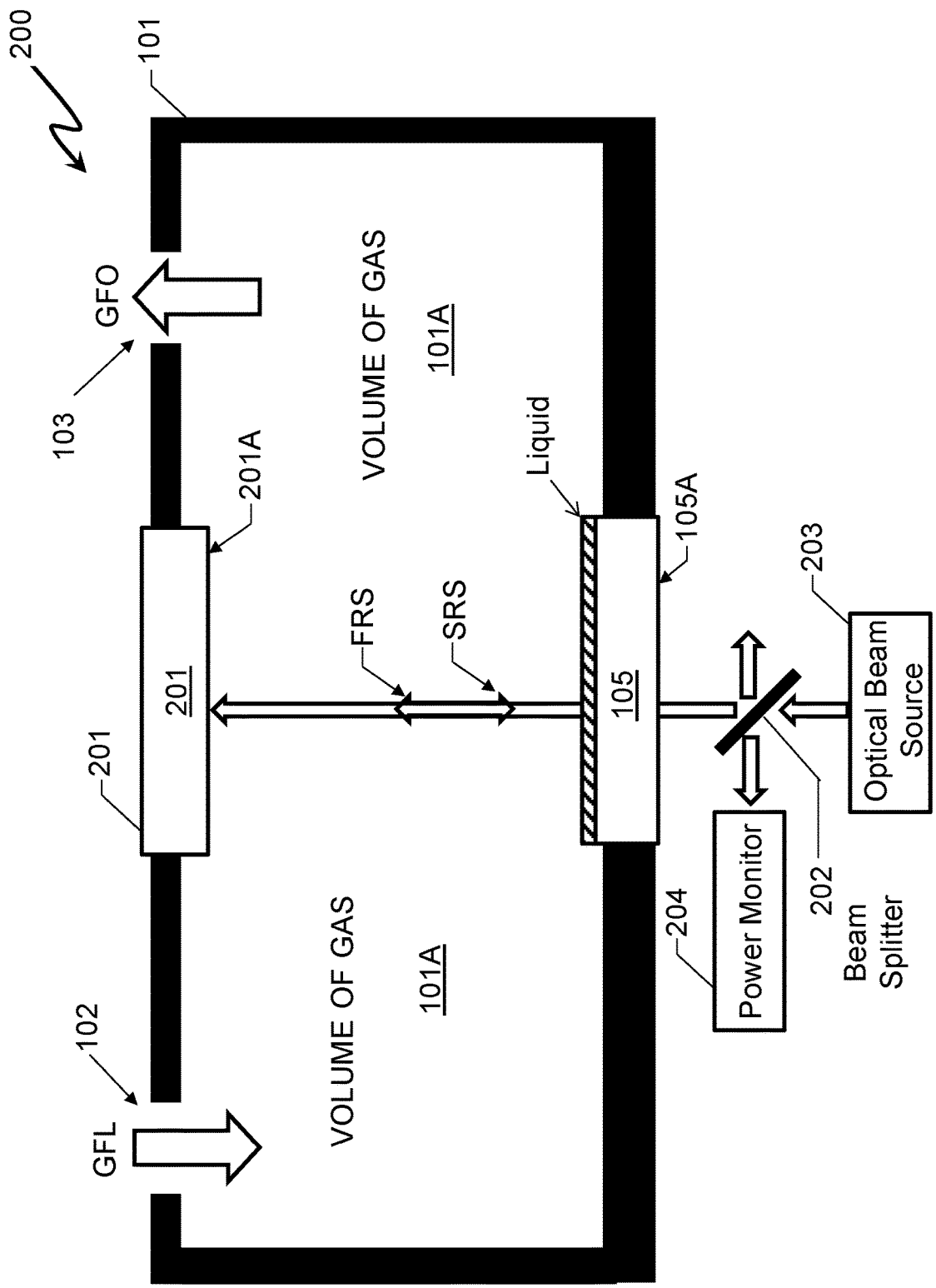
FIG. 2B illustrates the FIG. 2A implementation, at a system state indicating high liquid content in the gas volume, including liquid on the optical element surface.

In an example operation, as opposed to having an optical element surface facing a gas volume, that propagates optical beam with multiple traversal through the gas volume, to a spectral analysis apparatus, for detection by a graphically illustrated processor, for systems and methods for detecting and monitoring liquids within a gas, according to various aspects. FIG. 2B illustrates the FIG. 2A implementation, at a system state indicating liquid content in the gas volume, including liquid on the optical element surface.

Figure 3B:
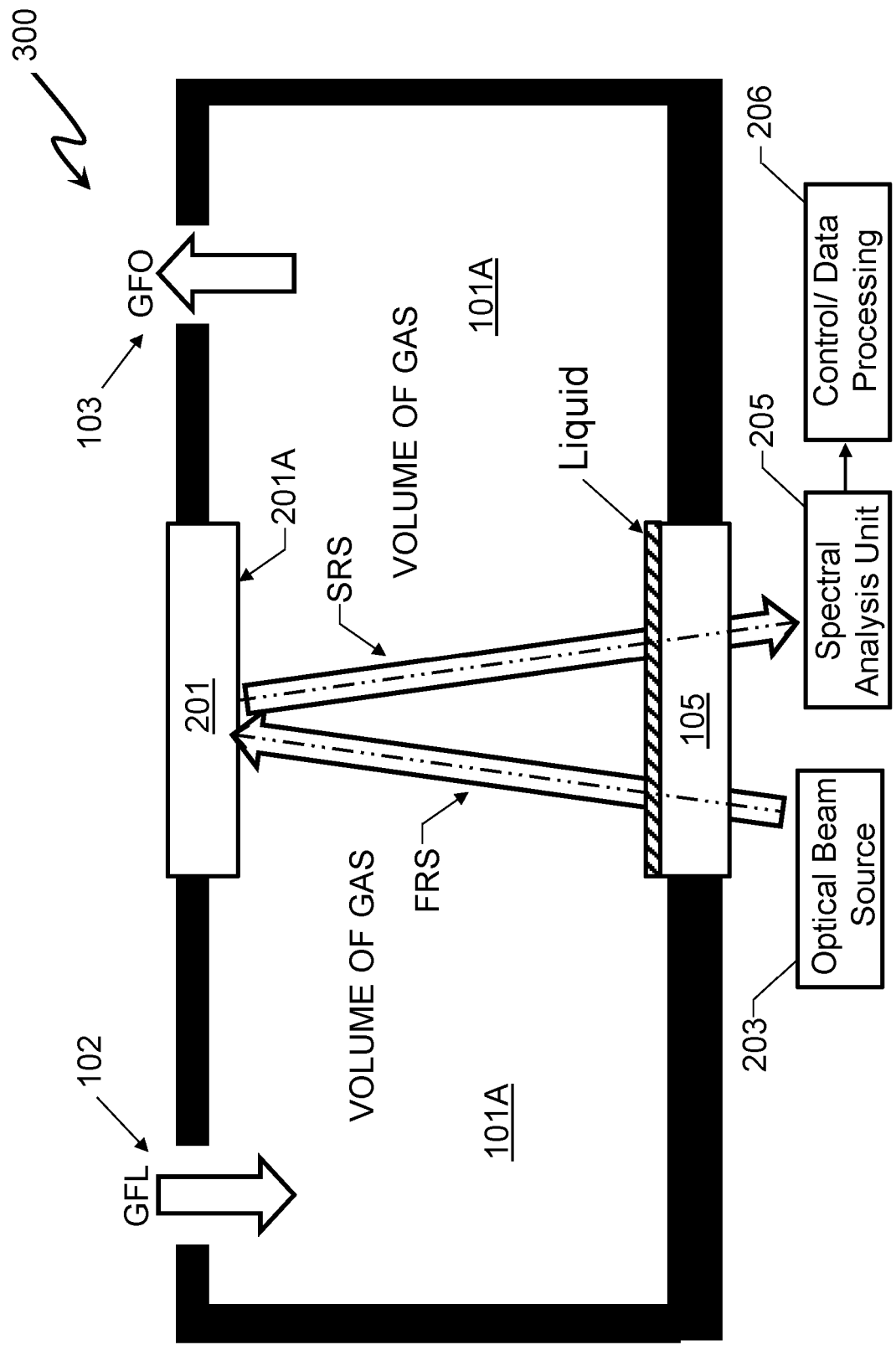
FIG. 3B illustrates the FIG. 3A implementation at a system state indicating high liquid content in the gas volume, including a liquid on the optical element surface.

FIG. 3A is a cut-away projection of a system 300, which is one example variation of the FIG. 2A-2B implementation. In the system 300 the optical beam source 203 is configured to transmit the optical beam such that the first ray segment FRS is incident on the mirror surface 201A at an angle (visible in FIG. 3A but not separately labeled), as opposed to the normal incidence provided by the system 200. The second ray segment SRS reflects from the mirror surface 201A at the same angle, and passes through the volume of gas, through the first optical element 105, to the reception surface of spectral analysis unit 205. The first ray segment FRS and the second ray segment SRS are therefore not parallel. Also, due to the respective angles of the first ray segment FRS and the second ray segment SRS, the optical beam source 203 and the reception surface of the spectral analysis unit 205 must be laterally spaced by distance (visible in FIG. 3A but not separately labeled). The system 300 can therefore provide one alternative multiple traversal propagation through the gas volume. FIG. 3B illustrates the FIG. 3A implementation at a system state indicating high liquid content in the gas volume, including a liquid on the optical element surface.

Figure 4B:
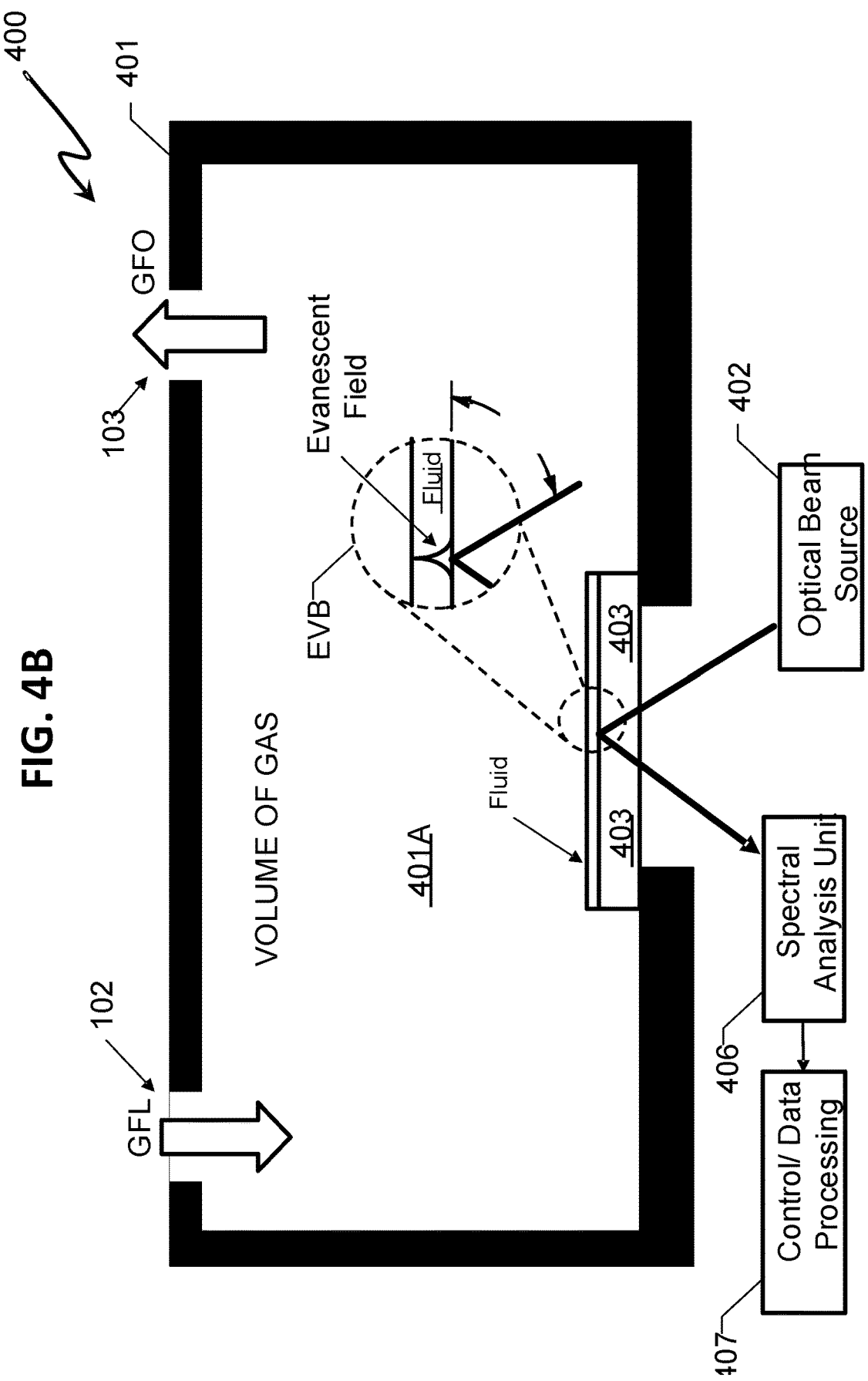
FIG. 4B illustrates the FIG. 4A implementation at a system state indicating high liquid content in the gas volume, including liquid on the optical element surface.

FIG. 4A is a cut-away view of one alternative implementation, providing a system 400. The system 400 can propagate an optical beam from an optical beam source 402 to an outer surface 403A of an optical element 403, through the optical element 403 to an element surface 403B facing gas content of a chamber interior 401A within a chamber housing 401. The refractive index of the optical element 403 relative to the refractive index of the gas within the chamber interior 401A can establish a refractive interface and a corresponding beam induced evanescent tail (visible in FIG. 4B, which is described later) that can vary with surface liquid. The refractive interface of the optical element 403 and the angle of incidence $\theta_1$ can be such that a non-absorbed optical beam NB can reflect back into and through the optical element 403 to a spectral analysis 406 and processing 407 illustrated by a graphical schematic. FIG. 4B illustrates the FIG. 4A implementation at a system state indicating liquid content in the gas volume, including liquid on the optical element surface 403B. The indication can be via a particular interaction of the evanescent tail with liquid on the optical element surface 403B. The interaction can cause a detectable absorption/loss of some of the optical signal, indicating presence of liquids.

Example practices of systems and methods can include detection of oil and/or water in natural gas streams. Natural gas can undergo phase transition, creating liquids, due to a number of different reasons. These reasons can include increasing pressure, decreasing pressure, and decrease in temperature of the gas. Aspects of the present disclosure can be used for such applications. For example, the optical beam can be passed through the gas. In another aspect, the optical beam can be passed through surface(s) of the optical element that is (are) exposed to the gas stream. The beam, after it travels through the gas, can be monitored at wavelengths corresponding to hydrocarbon and/or water absorption. Many different wavelengths can be monitored. In some applications, monitoring can be limited to, or can focus on particular wavelengths of interest. For example, hydrocarbons can absorb strongly around the 3.1-3.5 μm region. In some applications, monitoring this spectral region, as well as wavelengths corresponding to the optical absorption of water (such the ~2.8 μm) or alcohols, can provide benefits such as observation and detection of a change in the signal of one or several of these spectral regions, as condensation takes place. The change in the intensity of any of these spectral regions corresponds to the presence of the corresponding material on the surface of the optical element or in the gas phase.

Additional spectral regions can be monitored for potential condensation by vapors which can absorb radiation in those regions. For example, the region around 10 μm, corresponding to the C—O bonds, can be monitored. Absorption in this region can indicate presence of compounds with C—O bond, such as alcohols. As methanol can be a contaminant in natural gas, monitoring in this region can be used for detection of condensate that has methanol in it.

Alternatively, the optical signal can be taken to a spectrometer with a spectral region of interest. Then the presence of many different compounds in the condensate can be monitored concurrently. Example spectral regions of interest can include 0.5 μm to 12 μm, as this spectral area has absorption lines that can indicate the composition of various condensates. It will be understood that these are only examples and, in general, any spectral region, even in the <0.5 μm region, can be monitored for spectral signatures corresponding to potential condensate material exist in that region.

Specific material composition of the optical elements is not necessarily critical to systems and methods according to this disclosure. One selection guideline can be substantial transparency in the spectral regions that the reflected beam is to be monitored. The meaning of "substantial" can depend, at least in part, on the sensitivity of the spectral analysis unit. Since the Infrared spectral region exhibits very strong absorption for many molecules and also exhibits rich spectral features for most molecules, materials that are somewhat transparent in the Infrared spectral region are particularly useful as the optical element in systems and methods according to this disclosure.

In another implementation, a bare, unclad optical fiber can be used the optical element. Since optical signal propagates through an optical fiber by going through many internal reflections, the optical power can be attenuated if there is material, e.g., liquid, condensed on that fiber. By bending the fiber, the angle of incidence can be increased and the electrical field due to the optical signal can penetrate through the optical fiber more than if the optical fiber was straight. In such an implementation, when a gas has entrained liquid in it, or undergoes a phase transition and creates liquid, the liquid can condense on the surface and the presence of the liquid can be detected as described above.

Figure 5A:
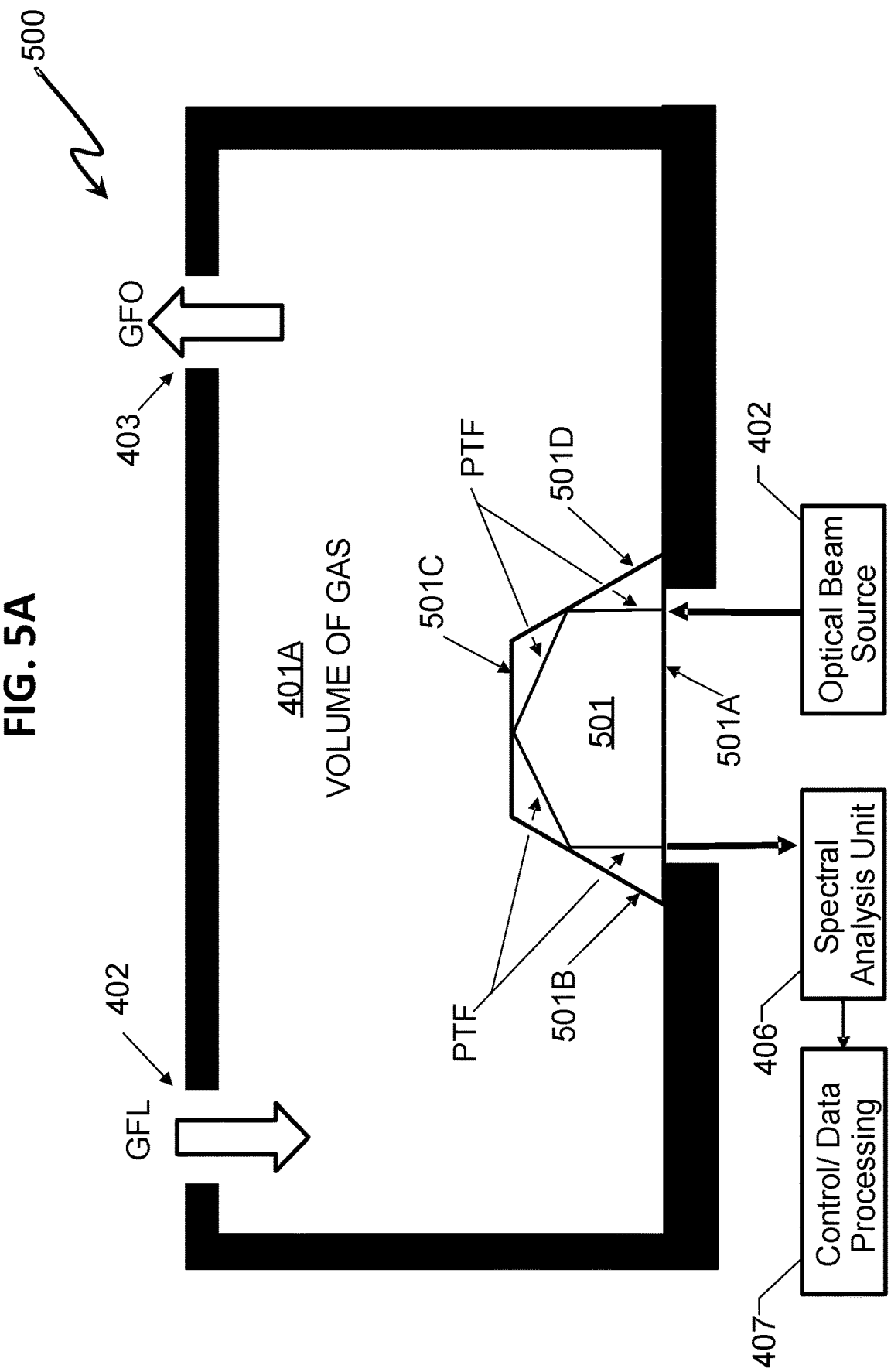
FIG. 5A is a cut-away view of one alternative implementation, which can propagate an optical beam through a multi-faced optical element, with a plurality of faces being toward the gas volume, the propagation being a sequence of reflections, each from another of the element faces, each reflection effected in part by a refractive interface and corresponding beam induced evanescent tail, both of which can vary according to surface liquid, to a spectral analysis and processing illustrated by a graphical schematic, for a multiple evanescent tail based monitoring and detection of liquids within a gas, in systems and methods according to various aspects.
Figure 5B:
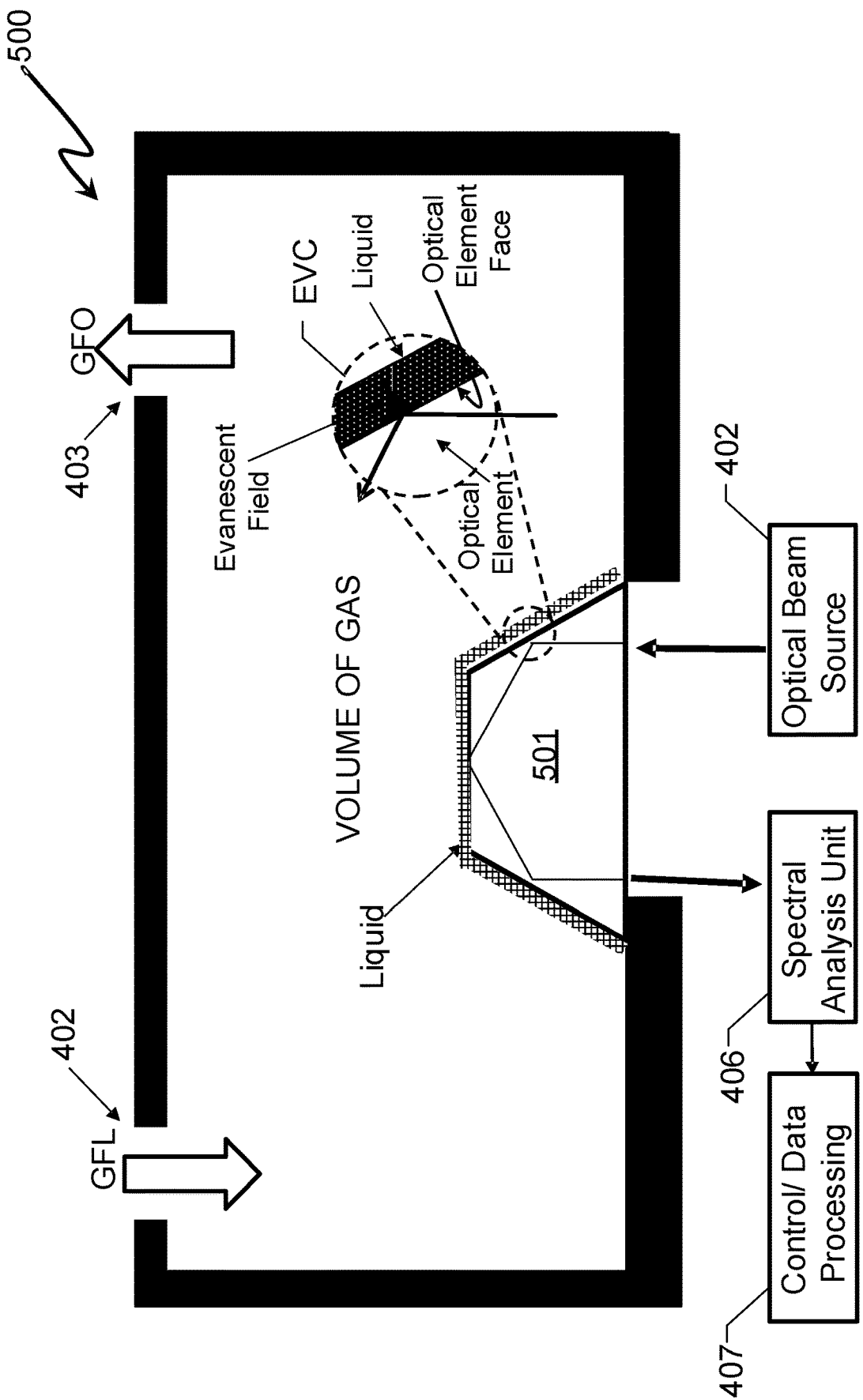
FIG. 5B illustrates the FIG. 5A implementation at a system state indicating high liquid content in the gas volume, including liquid on the optical element's multiple faces.

FIG. 5A is a cut-away view of one alternative implementation providing a system 500, which can propagate an optical beam through a multi-faced optical element 501, with one or more faces, e.g., 501B, 501C, and 501D, facing the gas volume. The propagation can include entering at face 501A, followed by a sequence of reflections forming a path PTF, each reflection being from another of the element faces, each reflection effected in part by a refractive interface and corresponding beam induced evanescent tail, both of which can vary with the wavelength of the light, the index of the optical elements, and the angle of incidence, to a spectral analysis and processing illustrated by a graphical schematic, for a multiple evanescent tail based monitoring and detection of liquids within a gas, in systems and methods according to various aspects. FIG. 5B illustrates the FIG. 5A implementation at a system state indicating high liquid content in the gas volume, including liquid on the optical element's multiple faces.

Figure 6A:
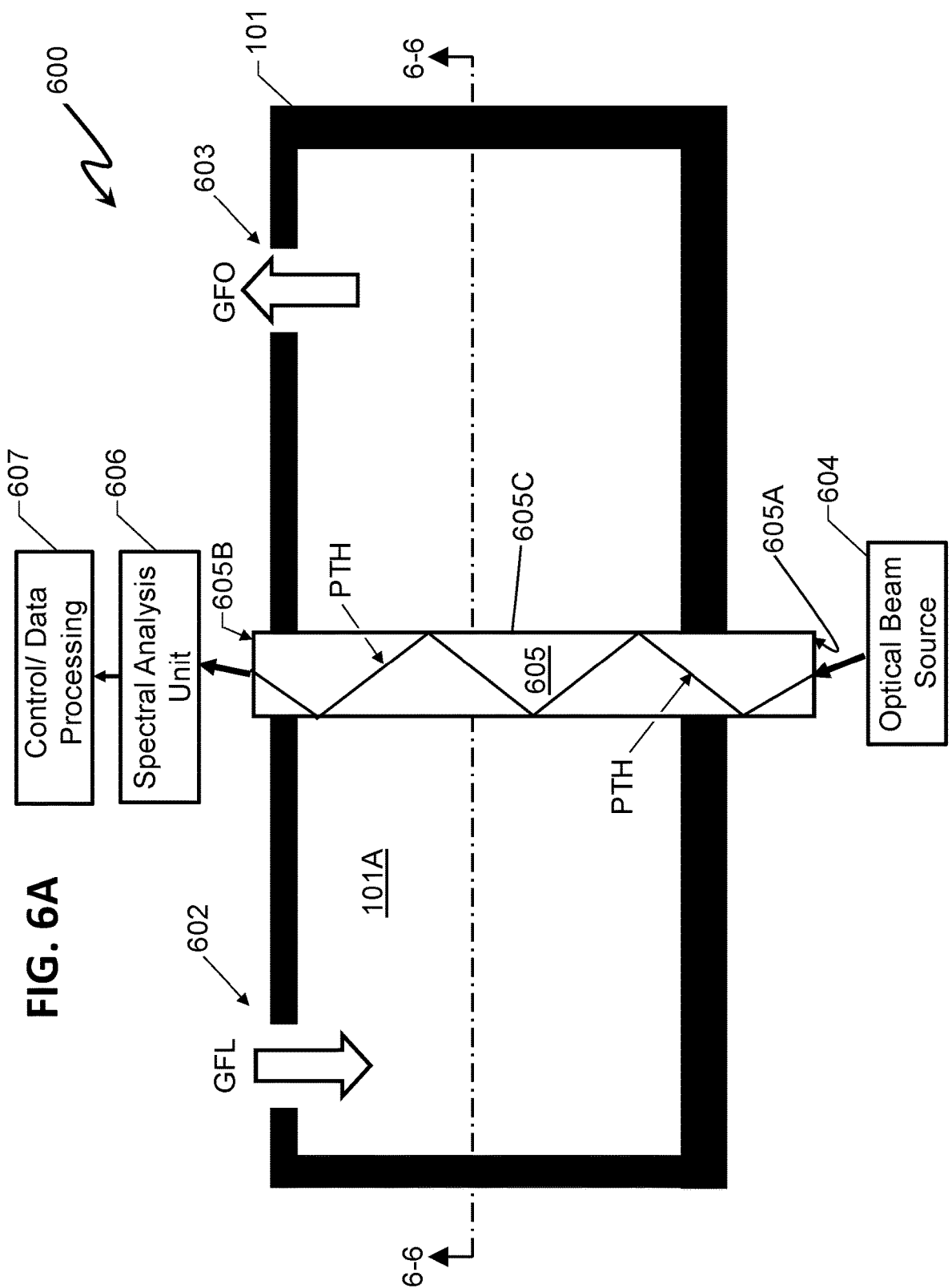
FIG. 6A is a cut-away view of one alternative implementation for systems and method according to this disclosure, featuring propagation of an optical beam along a multi-reflection path within an optical fiber extending across the gas volume, providing a multiple evanescent tail based monitoring and detection of liquids within a gas.
Figure 6B:
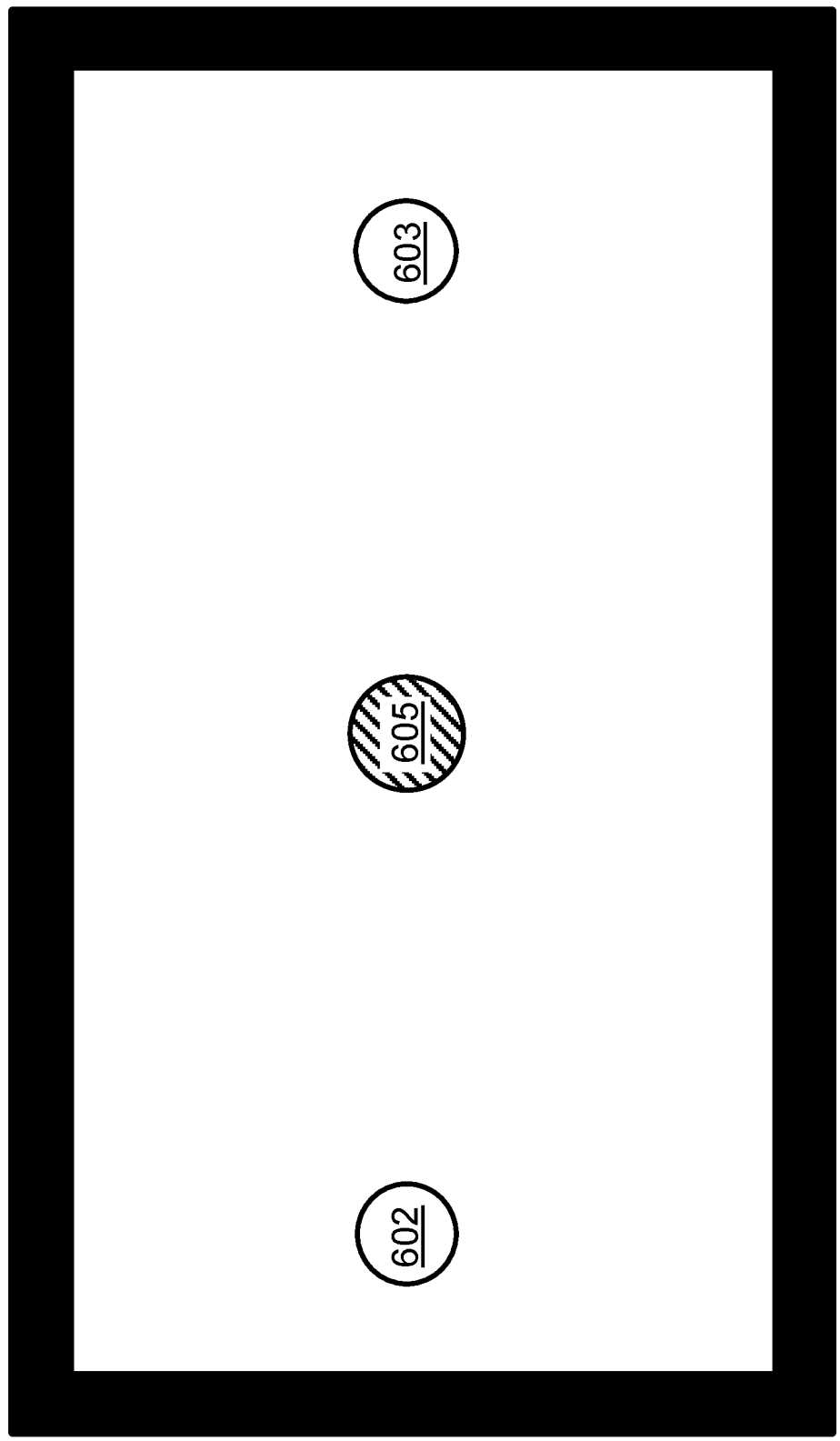
FIG. 6B is a cross-cut view of the FIG. 6A structure, seen from the FIG. 6A cross-cut projection plane 6-6.
Figure 6C:
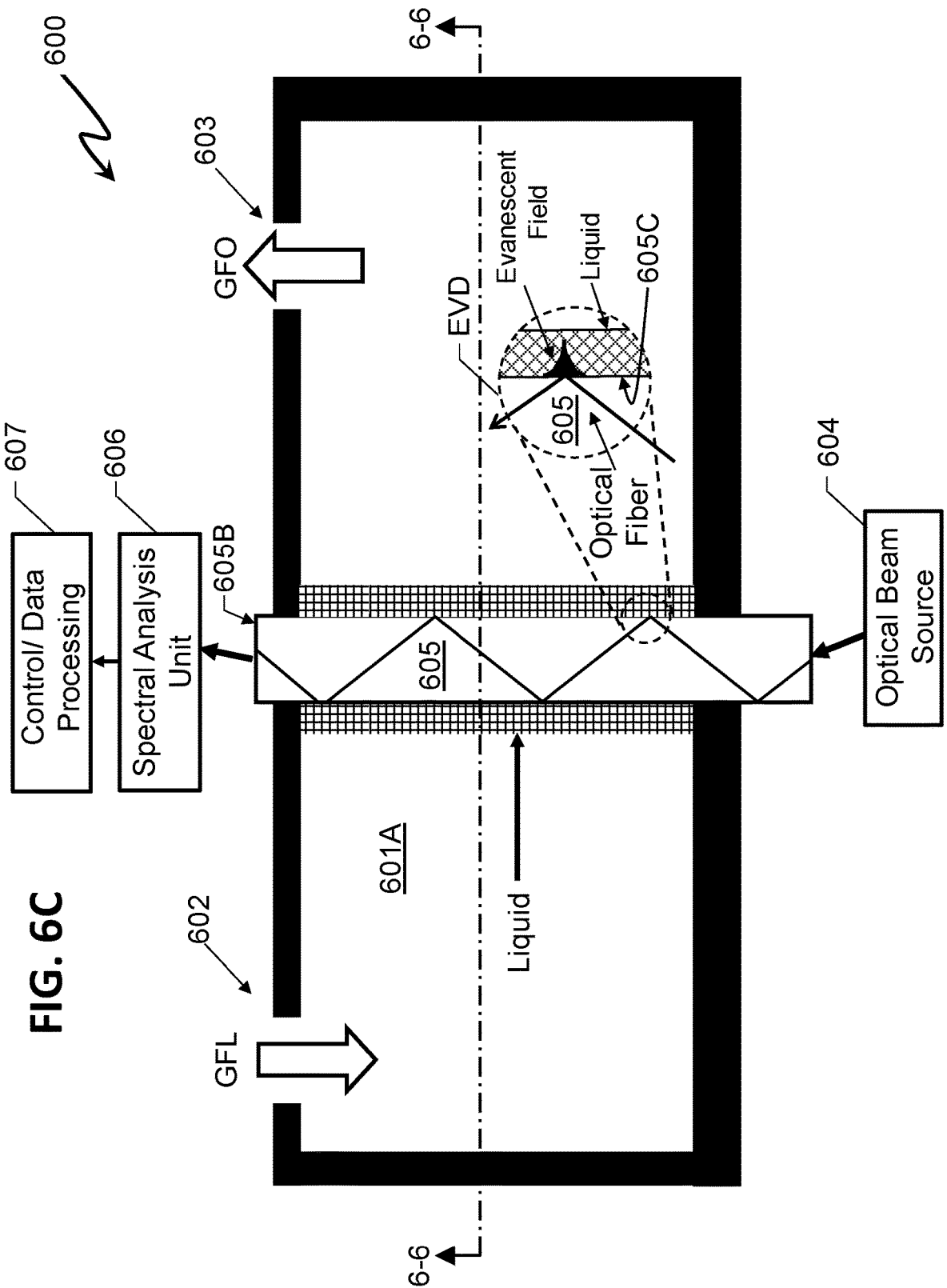
FIG. 6C illustrates the FIG. 6A implementation, at a system state indicating high liquid content in the gas volume, including liquid on the outer surface of the optical fiber.

FIG. 6A is a cut-away view of one alternative implementation, which will be referred to as "system 600." The system 600 can include a chamber housing 601 surrounding a chamber interior 601A, having gas inlet port 602 into the chamber 601A and gas outlet port 603 from the chamber 601A. The system 600 can propagate an optical beam from an optical beam source 604 into a first face 605A of an optical fiber 605 that can extend across the chamber interior 601A. The propagation can be along a multi-reflection path PTH within the optical fiber 605, and can exit from a second face 605B of the optical fiber 605. Each of the reflections forming the multi-reflection path PTH can be effected in part by a refractive interface between the outer surface 605C of the optical fiber 605 and the surrounding gas within the chamber interior 601A. FIG. 6B is a cross-cut view of the FIG. 6A structure, seen from the FIG. 6A cross-cut projection plane 6-6. FIG. 6C illustrates the FIG. 6A implementation, at a system state indicating high liquid content in the gas volume, including liquid on the outer surface of the optical fiber 604. FIG. 6D is the FIG. 6B cross-cut view of FIG. 6A structure, when in the FIG. 6C system state. Referring to FIG. 6D enlarged viewing area EVD, the refractive interface and corresponding beam induced evanescent tail can vary according to surface liquid on the outer surface 605C of the optical fiber 605. This can be detected by spectral analysis unit 606 and processing unit 607 illustrated by a graphical schematic. The system 600 can therefore provide a multiple evanescent tail based monitoring and detection of liquids within a gas, in systems and methods according to various aspects.

Figure 7A:
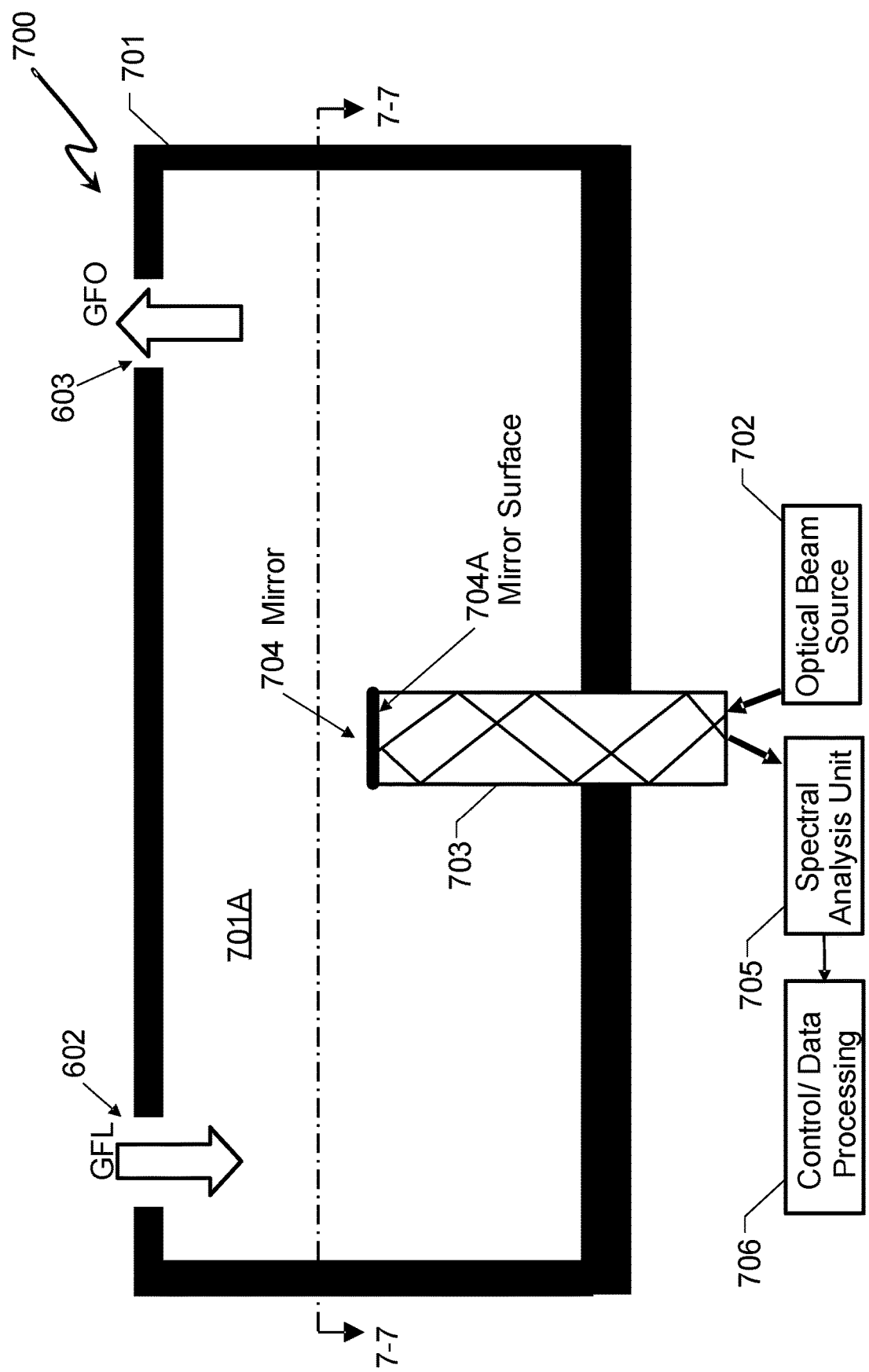
FIG. 7A is a cut-away view of one example variation of the implementation illustrated by the example of FIG. 6A, wherein the optical fiber, instead of extending across the gas volume, projects a distance into the gas volume, to a cap having an inward facing mirror surface, wherein the inward extending optical fiber can propagate an optical beam toward the mirror along a multi-reflection path comparable in part to that provided by the FIG. 6A implementation, and back from the mirror along another, opposite, multi-reflection path provided within the same inward projecting optical fiber, to a spectral analysis and processing illustrated by a graphical schematic, thereby providing another multiple evanescent tail based monitoring and detection of liquids within a gas, in systems and methods according to various aspects.
Figure 7D:
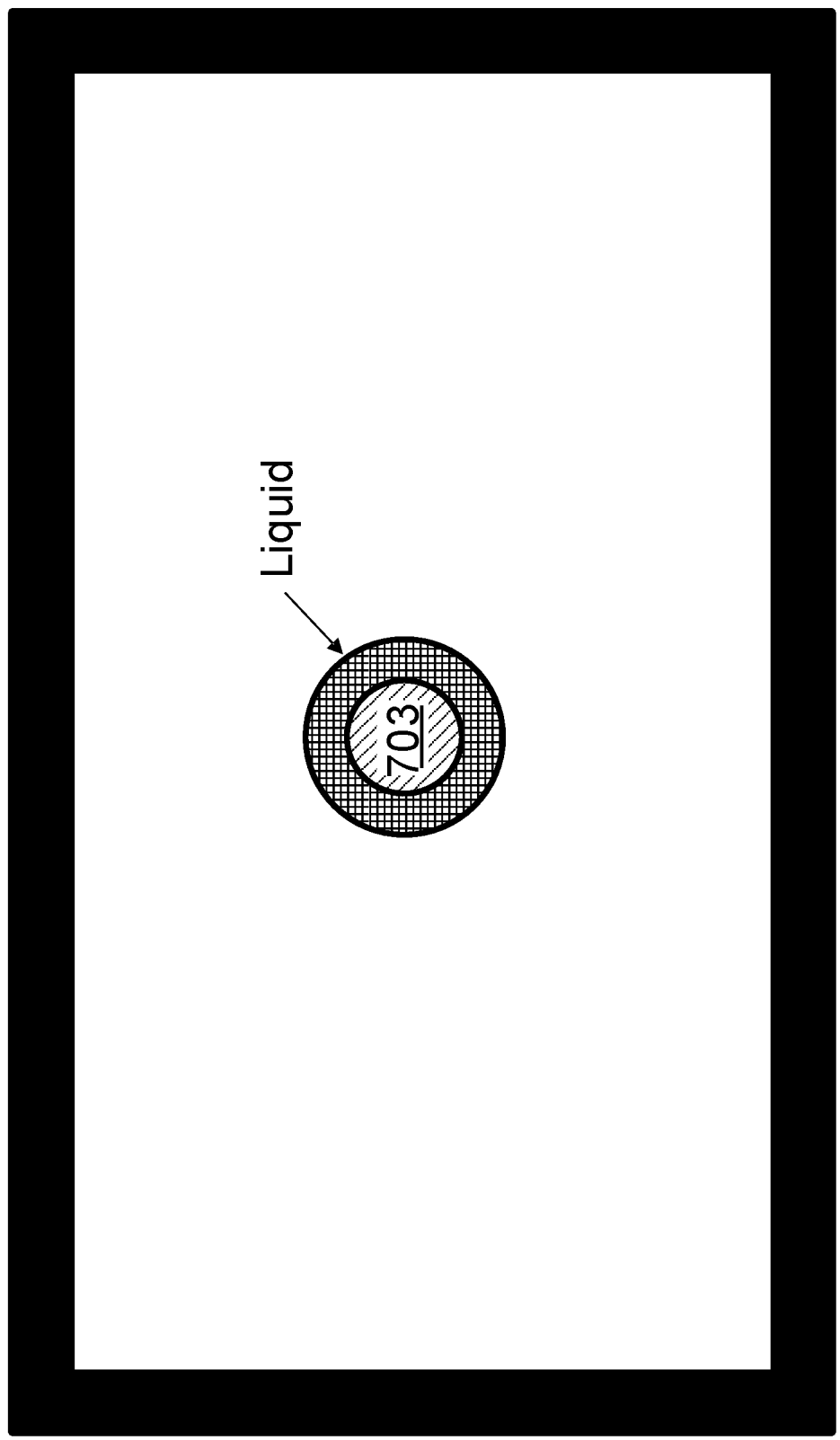
FIG. 7D is the FIG. 7B cross-cut view of FIG. 7A structure, when in the FIG. 7C system state.

FIG. 7A is a cut-away view of a system 700, which can be one example variation of the implementation illustrated by the example of FIG. 6A, wherein an inward projecting optical fiber 701, instead of extending across the gas volume as the system 600 optical fiber 605, projects a distance into the gas volume, to a cap 702 having an inward facing mirror surface 702A. The inward projecting optical fiber 701 can propagate an optical beam (visible in FIG. 7A, but not separately numbered) toward the mirror surface 702A, along a multi-reflection path (visible in FIG. 7A, but not separately numbered) comparable in part to the path PTH provided by the FIG. 6A implementation, and back from the mirror surface 702A along another, opposite, multi-reflection path (visible in FIG. 7A, but not separately numbered) provided within the same inward projecting optical fiber, to a spectral analysis 704 and processing 705, thereby providing another multiple evanescent tail based monitoring and detection of liquids within a gas, in systems and methods according to various aspects. FIG. 7B is a cross-cut view of FIG. 7A structure, seen from the FIG. 7A cross-cut projection plane 7-7.

Figure 8:
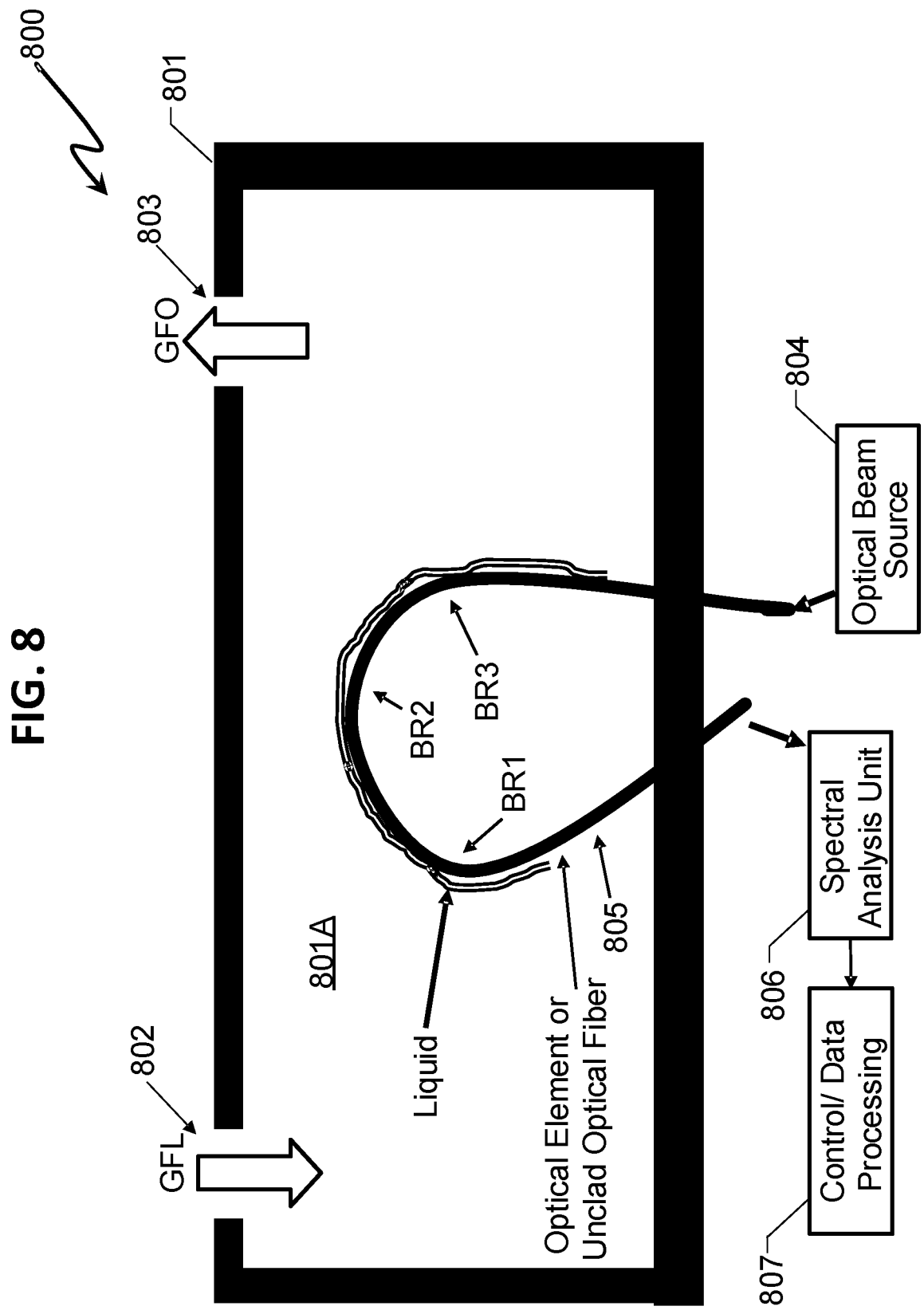
FIG. 8 is a cut-away view of another implementation, which can propagate an optical beam within a multiple-bend optical fiber that can extend into and within the gas volume, and out from the gas volume, providing an alternatively structured multi-reflection path, to another spectral analysis and processing illustrated by another graphical schematic, thereby providing another multiple evanescent tail based monitoring and detection of liquids within a gas, in systems and methods according to various aspects.

FIG. 8 is a cut-away view of system 800, which can include a measurement chamber housing 801 surrounding a chamber interior 801A, having a gas inlet port 802 and a gas outlet port 803. The system 800 can include an optical beam source 804 generating an optical beam that propagates within a multiple-bend optical fiber 805 (exemplary bends labeled BR1, BR2, and BR3), that can extend into and within the gas volume, and out from the gas volume. The system 800 can provide an alternatively structured multi-reflection path, to another spectral analysis 806 and processing 807 illustrated by another graphical schematic, thereby providing another multiple evanescent tail based monitoring and detection of liquids within a gas, in systems and methods according to various aspects.

Figure 9:
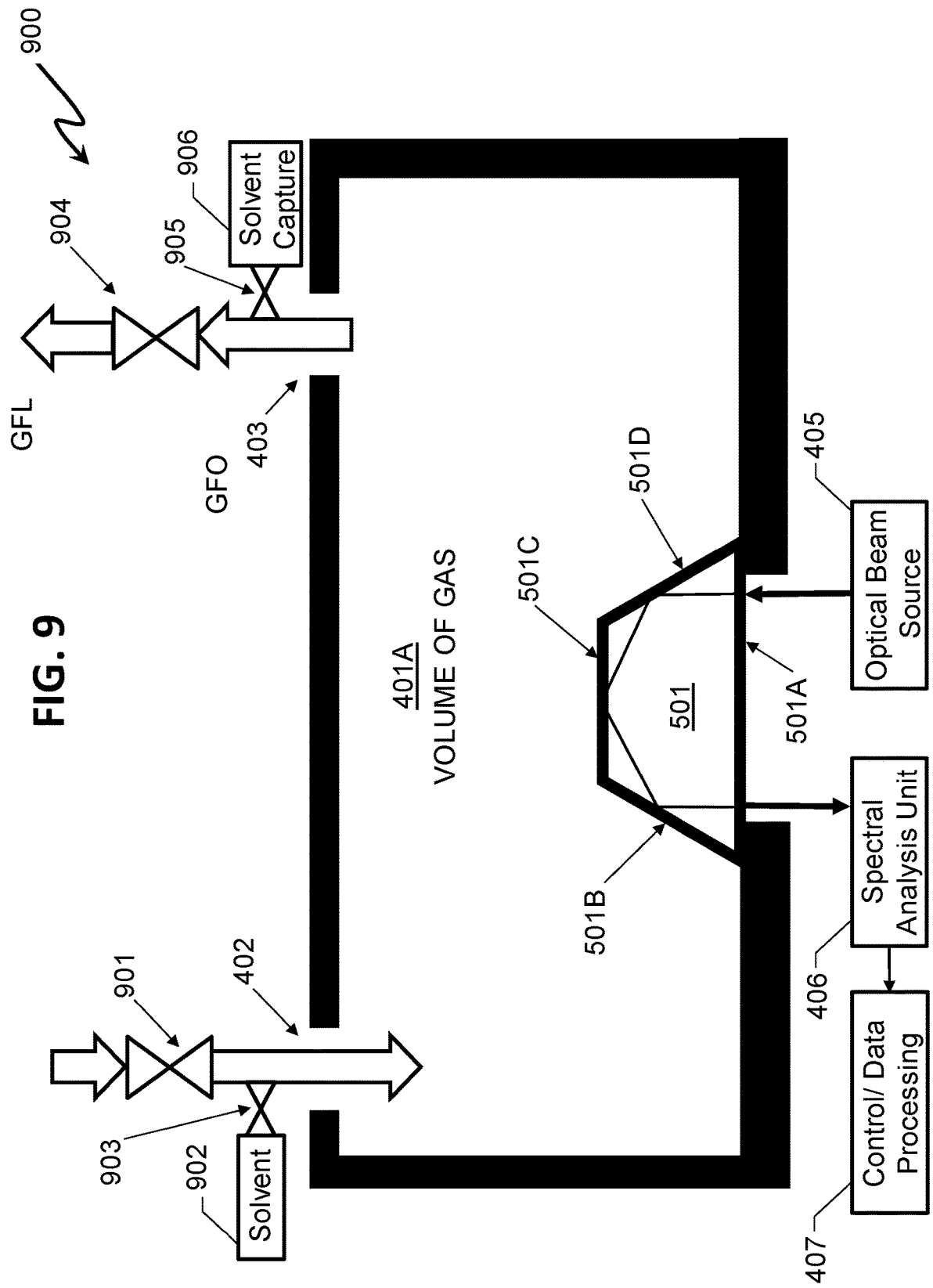
FIG. 9 is a cut-away view of an implementation, shown as a modification of the system of FIGS. 5A-5B, which includes structure configured to provide cleaning of the measurement chamber and optical element surface facing therein.

In an aspect, implementations of one or more systems in accordance with this disclosure can include structure configured to provide cleaning of the measurement cell. Such cleaning can provide, for example, removal of viscous liquids trapped or otherwise lingering in the measurement cell. FIG. 9 shows one implementation 900. The implementation 900 is shown as a modification of the FIG. 5A-5B system 500, but this is only for purposes of example. The solvent cleaning aspects of implementation 900 can be adapted, for example, to systems described in reference to FIG. 1, 2A, 2B, 3A, 3B, 4A, 4B, 6A-6D, 7A-7D, or 8.

Referring to FIG. 9, the implementation 900 can include an input gate valve 901 at the input port, e.g., gas inlet port 402 of the FIG. 5A-5B system 500, in combination with a solvent tank or reservoir 902 connected to the inlet port 402 via a solvent inlet port valve 903. The system 900 can include an outlet gate valve 904 at the outlet port 403, and a solvent vent or outlet valve 905 connecting the outlet port 403 to an expended solvent reservoir 905. Example solvents can include, but are not limited to, water, Ethane, Propane, Butane, Pentane, Hexane, Heptane, Nonane, Acetone, or Alcohol, or various combinations and sub-combinations thereof.

Operations of automatic cleaning can include, but are not limited to, closing the inlet gate valve 901 and the outlet gate valve 904, in combination with opening the solvent inlet port valve 903 and opening the solvent vent or outlet valve 905. The described operations can pass the solvent through the interior chamber 401, cleaning all surfaces exposed therein. Configurations can perform the cleaning on per-determined intervals (e.g., every morning, or twice or more per day, or one alternating days). Configurations can include automatic cleaning based, at least in part, on determination of residual contamination. Configuration can also include remote manual instantiation of cleaning, for example, based on the above-described determination of residual contamination. Implementations can provide a cleaning cycle that can include switching the source from the sample stream to the solvent, then switching from the solvent back to the sample stream, whereupon measurement and determination of the presence of liquid can resume.

Figure 10:
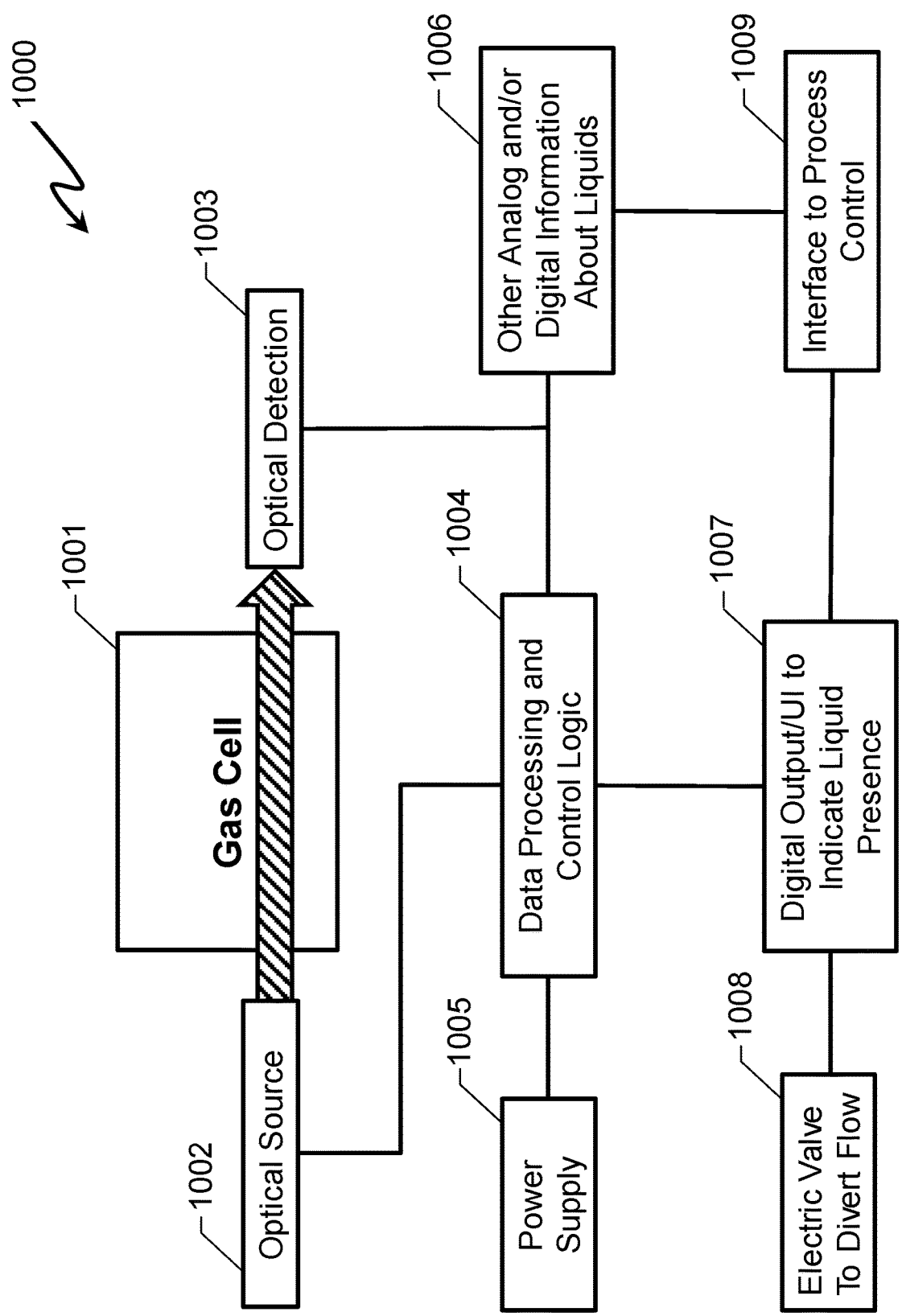
FIG. 10 is a functional block diagram of one exemplary implementation of a processing and control system.

FIG. 10 is a functional block diagram of one exemplary implementation of a processing and control system 1000. Control electronics can include analog and digital signal generators, signal amplifiers, filters, and digital processors with control software. The control electronics drives the optical source 1002, collects the optical signals at 1003, amplifies and processes the optical and electrical signals at 1004 to indicate, e.g., via 1009, presence or absence of liquids. If liquids are detected as present, information about the liquid can be sent, e.g., via block 1006, over analog and digital signals to the user (e.g., at 1007) to take action. A digital signal can also be used to drive one or multiple valves 1008 to redirect the flow to protect other equipment.

Another example application of systems and methods according to this disclosure can include detection of liquid water in compressed gas systems. Normal atmospheric air generally carries a given concentration of water vapor. If the normal air atmospheric is compressed, liquid water can form. This can arise because water vapor can undergo a phase transition, resulting in liquid water. There can be applications in which compressed air (or any other gas) needs to be devoid of liquids. Accordingly, they are dried before compression. Monitoring of the performance or efficacy of the drying operation can be beneficial.

While the foregoing has described what are considered to be the best mode and/or other examples, it is understood that various modifications may be made and that the subject matter disclosed herein may be implemented in various forms and examples, and that the teachings may be applied in numerous applications, only some of which have been described herein.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

It will be understood that the terms and expressions used herein have the ordinary meaning as is accorded to such terms and expressions with respect to their corresponding respective areas of inquiry and study except where specific meanings have otherwise been set forth herein.

Relational terms such as first and second and the like may be used solely to distinguish one entity or action from another without necessarily requiring or implying any such first, second relationship or order between such entities or actions.

The terms "comprises," "comprising," and variations thereof, are intended to cover a non-exclusive inclusion, such that a process, method, article, or apparatus that comprises a list of elements does not include only those elements but may include other elements not expressly listed or inherent to such process, method, article, or apparatus.

An element preceded by "a" or "an" does not, without further constraints, preclude the existence of additional identical elements in the process, method, article, or apparatus that comprises the element.

What is claimed is:

1. A method for determining whether a liquid is carried by a gas, the method comprising:
    passing an optical beam, from an optical source, through a volume of the gas, to a reception surface;
    applying a spectroanalysis to the optical beam as received at the reception surface, and outputting a corresponding spectroanalysis signal; and
    determining, based on the output spectroanalysis signal, whether a liquid is carried by the volume of the gas.

2. The method of claim 1, wherein passing the optical beam is a first passing the optical beam, and the first passing the optical beam is configured to pass the optical beam, for a first duration of time, through the optical element to the reception surface, and wherein the method further includes:
    performing a measurement, the measurement including a second passing the optical beam, for a second duration of time, and correspondingly repeating the spectroanalysis;
    determining, based on the output spectroanalysis signal corresponding to the measurement, whether the liquid is carried by the volume of gas; and
    repeating the performing step and the corresponding determining step, based on the measurement's output spectroanalysis signal, until in the determining step it is determined that the liquid is carried by the volume of gas,
    wherein:
        no temperature modification is applied to the propagation path during the repeating of the performing step the measurement and,
        at each repeat, determining based on the measurement output spectroanalysis signal, whether the liquid is carried by the volume of the gas.

3. The method of claim 1, wherein passing the optical beam is configured such that:
    the optical beam propagates along a propagation path from the optical source, through the volume of the gas, to the reception surface, and
    the propagation path includes multiple traversals within the volume of the gas.

4. The method of claim 3, wherein the propagation path includes:
    a first ray segment, from the optical source, through a region of the volume of the gas, to a mirror surface facing the region of the volume of the gas, and
    a second ray segment, from the mirror surface to through the region of the volume of the gas, to the reception surface.

5. The method of claim 4, wherein: the first ray segment and the second ray segment are not parallel.

6. The method of claim 1, wherein the optical beam is generated by a tungsten lamp, by a thin-film resistor, a light-emitting diode, or a laser.

7. The method of claim 1, wherein the optical path includes an optical element having a surface facing the volume of the gas, and wherein the method further comprises:
    monitoring a temperature of the optical element.

8. The method of claim 7, wherein:
    the optical element is an optical fiber, and
    monitoring the temperature of the optical element is based on a Fiber-Bragg Grating written onto the said optical fiber.

9. The method of claim 1, wherein:
    the liquid includes an alcohol,
    applying the spectroanalysis to the optical beam includes passing the received optical beam signal through one or more optical band-pass filters, and detecting the respective outputs of the one or more optical band-pass filters,
    the one or more optical band-pass filters are configured with an optical band-pass between 9.8 µm and 10.5 µm, and
    determining whether the alcohol is carried by the volume of the gas is based on the respective outputs of the one or more optical band-pass filters.

10. The method of claim 1, wherein:
    the optical signal at the reception surface is detected using one or several band-pass filters, in combination with detectors, with the band-pass of the filters anywhere between 1.8 µm-2.3 µm and/or between 2.6-3.0 µm to indicate presence of a water.

11. The method of claim 1, wherein:
    the optical path includes an optical element having a surface facing the volume of the gas, and
    the optical signal at the reception surface is detected using one or several band-pass filters, in combination with detectors, with the band-pass of the filters being anywhere between 3.0-3.5 µm, and/or 5.5-8.5 µm to indicate presence of a hydrocarbon in a condensate on the surface of the optical element facing the volume of the gas.

12. An apparatus for determining whether a liquid is carried by a gas, the apparatus comprising:
   a measurement housing, configured to enclose a chamber, and to include a gas inlet port into the chamber and a gas outlet port from the chamber;
   an optical element, having a surface facing the chamber;
   an optical source, configured to pass an optical beam into the optical element in a direction to be incident on the surface facing the chamber;
   a spectroanalysis unit, configured to receive the optical beam subsequent to incidence on the surface facing the chamber, and output a corresponding spectroanalysis signal; and
   a processing unit configured to receive the output spectroanalysis signal and based thereon to determine whether a liquid is carried by a volume of the gas received into the chamber through the gas inlet port.

13. The apparatus of claim 12, wherein passing the optical beam is a first passing of the optical beam, and the first passing the optical beam is configured to pass the optical beam, for a first duration of time, through the optical element to the spectroanalysis unit, and wherein the apparatus further comprises a controller, the controller being coupled to the optical source, the spectral analysis unit, and the processing unit, and the controller being configured to cause the optical source, the spectral analysis unit, and the processing unit to:
   perform a measurement operation, the measurement operation including
      the optical source passing the optical beam as a second passing of the optical beam, for a second duration of time, into the optical element in the direction to be incident on the surface facing the chamber and to be received for the second duration of time by the spectroanalysis unit, and the spectral analysis unit outputting for the second duration of time a another corresponding spectroanalysis signal, and
      the processing unit performing a determining operation, based on the output another corresponding spectroanalysis signal, whether the liquid is carried by the volume of gas;
   repeat the measurement operation and the corresponding determining, operation based on the output another corresponding spectroanalysis signal for each repeat, until the determining operation determines the liquid is carried by the volume of gas,
   wherein each repeat includes determining based on the output another corresponding spectroanalysis signal, whether the liquid is carried by the volume of gas.

14. A method for determining whether a liquid is carried by a gas, the method comprising:
   transmitting an optical beam into an optical element, the optical element having a surface that faces a volume of the gas, wherein the optical beam enters the optical element at an entry location on the optical element, is incident on the surface that faces the volume of the gas, and exits the optical element as an exit beam from an exit location on the optical element;
   applying a spectroanalysis to the exit beam; and
   determining, based on a result the spectroanalysis, whether the liquid is carried by the volume of the gas.

15. The method of claim 14, wherein the optical beam passes from the input location to the exit location along an internal propagation path, the internal propagation path including a first ray line from the entry point to the surface that faces the volume of the gas and a second ray line from the surface that faces the volume of gas to the exit location.

16. The method of claim 14, wherein the method further includes:
   performing a measurement, the measurement including passing the optical beam for another duration of time, and correspondingly applying another spectroanalysis and outputting a spectroanalysis result;
   determining, based on the spectroanalysis result, whether the liquid is carried by the volume of the gas; and
   repeating the performing step and the corresponding determining step, until the determining step determines the liquid is carried by the volume of the gas,
   wherein:
      no temperature modification is applied to the optical element during the repeating the performing step and,
      at each repeat, determining based on the spectroanalysis result whether the liquid is carried by the volume of the gas.

17. The method of claim 14, wherein the optical element is diamond, sapphire, zirconium oxide, zinc selenide, zinc sulfide, silicon, optical glass or germanium, or any combination or sub-combination thereof.

18. The method of claim 14, wherein the optical element is an optical fiber.

19. The method of claim 14, wherein applying the spectroanalysis to the exit beam includes applying a spectrometer that includes a gradient optical filter in combination with a diode-array detector.

20. The method of claim 14, wherein applying the spectroanalysis to the exit beam includes applying Fourier Transform Infrared Spectroscopy (FTIR).

* * * * *